(12) United States Patent
De Bont et al.

(10) Patent No.: US 12,171,905 B2
(45) Date of Patent: *Dec. 24, 2024

(54) MEDICAL IMPLANT COMPONENT COMPRISING A COMPOSITE BIOTEXTILE

(71) Applicant: DSM IP Assets B.V., Heerlen (NL)

(72) Inventors: Nicolaes Hubertus Maria De Bont, Echt (NL); Noel L. Davison, Echt (NL); Mandy Maria Jozefina Wiermans, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 606 days.

This patent is subject to a terminal disclaimer.

(21) Appl. No.: 17/430,734

(22) PCT Filed: Mar. 2, 2020

(86) PCT No.: PCT/EP2020/055415
§ 371 (c)(1),
(2) Date: Aug. 13, 2021

(87) PCT Pub. No.: WO2020/178227
PCT Pub. Date: Sep. 10, 2020

(65) Prior Publication Data
US 2022/0023501 A1 Jan. 27, 2022

(30) Foreign Application Priority Data
Mar. 1, 2019 (EP) .................................. 19160368

(51) Int. Cl.
*A61L 27/34* (2006.01)
*A61L 27/16* (2006.01)
(Continued)

(52) U.S. Cl.
CPC ............... *A61L 27/34* (2013.01); *A61L 27/16* (2013.01); *A61L 31/048* (2013.01); *A61L 31/10* (2013.01);
(Continued)

(58) Field of Classification Search
None
See application file for complete search history.

(56) References Cited

U.S. PATENT DOCUMENTS

| 4,693,720 A | 9/1987 | Scharnberg et al. |
| 5,178,630 A | 1/1993 | Schmitt |

(Continued)

FOREIGN PATENT DOCUMENTS

| JP | 5111505 A2 | 5/1993 |
| WO | 2019197353 A1 | 10/2019 |

OTHER PUBLICATIONS

Tang, Z.G., Microstructural evaluation of an elastomeric composite, Colloids and Surfaces B: Biointerfaces, 2000, 19-29, 19.
(Continued)

*Primary Examiner* — Arti Singh-Pandey
(74) *Attorney, Agent, or Firm* — NIXON & VANDERHYE P.C.

(57) ABSTRACT

Disclosed herein is a medical implant component comprising a composite biotextile, which biotextile comprises i) a polyolefin fibrous construct comprising at least one strand with titer of 2-250 dtex, tensile strength of at least 10 cN/dtex and comprising high molar mass polyolefin fibers and ii) a coating comprising a biocompatible and biostable polyurethane elastomer comprising a polysiloxane segment and/or having one or more hydrophobic endgroups, wherein the polyurethane coating is present on at least part of the surface of the biotextile and in an amount of 2.5-90 mass % based on composite biotextile. Such composite biotextile,
(Continued)

like a partly coated woven fabric, shows an advantageous combination of good biocompatibility, especially hemocompatibility, high strength and pliability, and laser cuttability; allowing to make pieces of fabric having well-defined regular edges that have high suture retention strength. The invention also provides a method of making said composite biotextile. Further embodiments concern the use of such biotextile in or as medical implant component for an implantable medical device and the use of such medical implant component in making an implantable medical device; such as in orthopedic applications and cardiovascular implants. Other embodiments include such medical devices or implants comprising said medical implant component.

20 Claims, 3 Drawing Sheets

(51) Int. Cl.
*A61L 31/04* (2006.01)
*A61L 31/10* (2006.01)
*D06N 3/00* (2006.01)
*D06N 3/14* (2006.01)

(52) U.S. Cl.
CPC ......... *D06N 3/0006* (2013.01); *D06N 3/0038* (2013.01); *D06N 3/14* (2013.01); *D06N 2211/18* (2013.01)

(56) References Cited

U.S. PATENT DOCUMENTS

| | | |
|---|---|---|
| 5,741,332 A | 4/1998 | Schmitt |
| 6,652,966 B1 | 11/2003 | Hin et al. |
| 2002/0065552 A1 | 5/2002 | Jayaraman et al. |
| 2003/0194935 A1 | 10/2003 | Schlomski et al. |
| 2006/0116713 A1* | 6/2006 | Sepetka ........... A61B 17/12145 606/200 |
| 2012/0021216 A1 | 1/2012 | Veillat et al. |
| 2013/0325117 A1 | 12/2013 | Bruchman et al. |
| 2014/0296962 A1 | 10/2014 | Cartledge et al. |
| 2014/0374002 A1 | 12/2014 | Lin |
| 2017/0354802 A1 | 12/2017 | Krautkremer et al. |
| 2022/0072199 A1* | 3/2022 | De Bont ................ A61L 27/16 |
| 2023/0310718 A1* | 10/2023 | Davison ................ A61L 27/18 424/424 |

OTHER PUBLICATIONS

International Search Report dated May 29, 2020.

* cited by examiner

2A

2B

3A

3B

4A

4B

MEDICAL IMPLANT COMPONENT COMPRISING A COMPOSITE BIOTEXTILE

CROSS-REFERENCE TO RELATED APPLICATIONS

This application is a U.S. national phase entry under 35 USC 371 of international application PCT/EP2020/055415, filed 2 Mar. 2020, which designated the US and claims priority to EP application Ser. No. 19/160,368.7, filed 1 Mar. 2019, the entire contents of each of which is hereby incorporated by reference in its entirety.

FIELD

The disclosed invention pertains to a biotextile, more specifically to a medical implant component based on a modified polyolefin fibrous construct, to methods of making such component, and to use of such component in making a medical implant.

BACKGROUND

The term medical textile is generally used for a flexible material made of a network of fibers, which is used outside the body and not in contact with circulating blood or open wounds; like bandages, dressings, eye patches, incontinence products, braces, surgical drapes, face masks, etc. Biotextile refers to non-viable, permanent or temporary, fibrous constructs like cables and textiles created from synthetic or natural fibers, which are used either in an internal (inside the body) or external (outside the body) biological environment as a medical device for the prevention, treatment or diagnosis of an injury or disease, and as such serve to improve the health, medical condition, comfort and wellness of the patient.

Examples of medical implants wherein a biotextile can be used include surgical sutures, hernia meshes, ligaments and tendons, and cardiovascular applications like patches, grafts and prosthetic heart valves. Requirements for fibers that can be used in implants relate to biocompatibility, biodegradability vs biostability, mechanical properties like strength, and purity (e.g. free from toxic substances, no surface contaminants like lubricants and sizing agents). Many surgical procedures that involve placing an implant can be performed using open or percutaneous/endoscopic surgical techniques. The latter minimal invasive approach is becoming more and more adopted due to clinical benefits such as faster recovery time of the patient. The increasing adoption rate of these types of procedures creates the need for a lower profile of the devices used, requiring biotextile products that also meet requirements of pliability; like compacting and compressing to fit within a narrow delivery system, without negatively affecting properties and performance of the textile or fabric in use. A fabric is a flexible textile made by interlacing one or more strands of fibers, for example by knitting, weaving or braiding; and generally, the textile has a thickness much smaller than other dimensions like length and width.

Examples of biocompatible and biostable fabrics include those made from polyolefin-based fibers; especially from thin, yet very strong monofilaments or multi-filament yarns made from ultra-high molecular weight polyethylene (UHMWPE). Such UHMWPE fibers are applied in or have been proposed for use in medical implants like sutures, meshes, (stent-)grafts and heart valves.

For biomedical use, a textile or fabric often needs to be cut to a smaller piece of desired size or shape and/or be connected to another (implant or body) component for example via stitching or suturing. Generally, at least cut edges of such piece of fabric require some form of stabilization to increase its fraying or raveling resistance and its suture retention strength. Suture retention represents the ability of the fabric to resist tearing or unraveling due to tensile forces acting on a suture that passes through the fabric, usually to fix the fabric to some other component of a medical device such as a metallic stent. There are many challenges to stabilizing a cut edge of biotextile used as a component of a permanent medical implant, particularly those implants delivered percutaneously and in direct blood contact. Specifically, disadvantages of typical stabilization techniques may include (i) additional profile of the component and device, thereby requiring a larger catheter to implant it, (ii) additional material that may not have optimal blood contact properties such as thrombogenicity, (iii) distortion of the cut edge biotextile morphology, (iv) insufficient bond strength of the stabilization material increasing the risk of embolization of foreign particulate in the blood stream, and (v) stiffening of the biotextile or reducing its pliability.

It is further known that physical properties like surface texture, roughness, porosity and pore size of a fabric have influence on interactions with bodily fluids and tissues; and that such properties may need to be adjusted for a given application to control e.g. clotting of blood, an innate inflammatory response, or tissue ingrowth.

Document U.S. Pat. No. 5,178,630 describes making a ravel-resistant woven synthetic vascular graft, i.e. a woven fabric made from polyester (polyethylene terephthalate, PET) yarns and incorporating a low melting fusible strand in the weave. After heat setting the fabric, the fusible component connects to neighboring other yarns and thus increases ravel resistance. The fusible strand may be a yarn formed from bicomponent filaments having a PET core and a lower melting polymer sheath. The document also describes a fabric with a fine low profile woven inner surface to promote smooth thin pseudointima formation and an external textured surface with yarn loops, like a velour surface, which texture would enhance tissue adhesion and ingrowth.

U.S. Pat. No. 5,741,332 relates to tubular soft tissue prostheses, like vascular grafts formed by weaving or braiding synthetic fibers. The document addresses problems such as fray-resistance of edges and controlling different porosities of internal and external surfaces. Multi-layered, three-dimensional braided structures are described, with either interlocking yarns connecting the layers or with separately formed layers being adhesively laminated. This approach would result in an inner layer with smooth surface and low porosity to prevent leakage and thrombus formation and an outer layer having a textured surface to enhance tissue ingrowth. The braided structure may further comprise a fusible material that is heat melted to bond to surrounding yarns to enhance ravel resistance and provide a graft more suitable for suturing to a body lumen. The braided structures are typically made from 20-1000 denier PET multi-filaments yarns and a lower melting fusible yarn.

U.S. Pat. No. 4,693,720 describes a surgical mesh comprising a woven fabric made from carbon fibers, to which—after having removed all non-biocompatible sizing that was present to enable fiber production—a first thin coating (or sizing) of a biodegradable polymer like polycaprolactone (PCL) is applied by solution coating to (re-)stabilize the fabric. A second coating layer is applied to the edges of the fabric using a solution of biodegradable polymer (e.g. PCL) with a higher concentration. The thus formed edging strip is indicated to be strong enough to support stitches or sutures when the device is surgically implanted. Alternatively, a polymer film strip may be applied to the edges and heated to melt coat the fabric edges.

In US2014/0374002 a method of making non-frayed, fused edges in a woven fabric is described; comprising directing heat on a section of the fabric for example with a nozzle expelling hot air, and then compressing the heated section to at least partially fuse the fibers. Subsequently, the fabric is cut at the fused sections, for example with a rotary knife, forming stabilized edges.

JP5111505 relates to making artificial blood vessels with good handleability and showing improved properties like sewing and fraying resistance. The document especially describes a prosthetic blood vessel made from ultrafine fibers of 0.8 dtex or less and 3-45 mass % (based on fibers) of a polymeric elastomer. More specifically, a tubular structure is formed from ultrafine fibers by weaving or other technique and elastomer is applied as a liquid to the structure by impregnating or coating, or preferably by thermally laminating a thin film. The elastomer does not fully cover fibers of the tubular structure and it is taught to apply the elastomer on the outside rather than on the inside of the tubular structure. Suitable polymeric elastomers include polyurethanes, polyureas, acrylics, styrene copolymers and natural rubber. In experiments, a tubular knitted structure was made from PET/polystyrene islands-in-sea fibers and the structure was then treated with trichloroethylene to remove the polystyrene component. The tubular fibrous construct was subsequently coated with a polyether urethane. The resulting structure showed good fraying resistance, sutureability and healing upon implanting in the aorta of dogs.

Despite the disclosures in the above documents, there still is a need for a polyolefin-based textile suitable for use in biomedical applications, which biotextile combines biocompatibility with properties like high pliability, cuttability, fraying resistance and suture retention strength.

SUMMARY

Objects of the present disclosure include providing such a polyolefin-based textile for use in biomedical applications, which biotextile combines biocompatibility, high pliability and properties like suitable fraying resistance and suture retention strength, including at an edge made by cutting the fabric; as well as providing a method of making such fabric.

The embodiments as described herein below and as characterized in the claims provide such biotextile that combines several properties making it suitable for use as a component in making medical devices, especially in cardiovascular implants. In accordance with an aspect of the invention, this disclosure provides a medical implant component according to claim 1, or a composite biotextile for use as a medical implant component, wherein the composite biotextile comprises A polyolefin fibrous construct made from at least one strand with titer of 2-250 dtex, tensile strength of at least 10 cN/dtex and comprising high molar mass polyolefin fibers; and A coating comprising a biocompatible and biostable polyurethane elastomer comprising a polysiloxane in soft segments and/or having hydrophobic endgroups; and wherein the polyurethane coating is applied to at least part of the surface of the fibrous construct, and is present in an amount of 2.5-90 mass % of the composite biotextile.

It was found that such composite biotextile of the invention can be cut by using a laser at a coated location to a desired size, e.g. for its intended use in or as a component of a medical implant, like as a graft material or as a valve leaflet; to result in a piece of biotextile with a well-defined and stable cut edge that shows improved fraying resistance and suture retention compared to the non-coated and laser-cut polyolefin fibrous construct. The inventors suggest, without wishing to be bound to any theory, that the polyurethane comprising the specific hydrophobic segments and/or endgroups properly coats and adheres to the polyolefin and that upon laser cutting the composite biotextile, the applied energy may shortly and locally increase the temperature to above the melting point of the polyurethane coating and of the polyolefin; resulting in polyurethane, especially TPU, locally melting and further flowing around and connecting fibers, while polyolefin fibers may not show noticeable melt flow under such conditions. Use of such polyurethane-coated polyolefin biotextile, for example a composite woven fabric, in an implant requiring improved fraying resistance is not an obvious choice, as an applied coating may deteriorate other properties of the fibrous construct, such as pliability, biostability, and importantly hemocompatibility. In addition, US2014/0296962 relating to prosthetic heart valves, describes a braided construct made from polyester yarn and coated with for example a polyurethane for stabilizing and reducing permeability for use as graft material. In this document, however, it is taught that laser cutting a non-coated braid results in a cut edge that is sealed to prevent fraying; and that when laser cutting is applied the need for any coating to stabilize the cut edge of the braid is reduced, or even eliminated.

Another advantage of the present composite biotextile is that by applying the coating at selected locations, the modified biotextile may show improved interaction or biocompatibility when it is used in a medical implant, like excellent hemocompatibility and reductions in calcification and/or tissue ingrowth, in addition to properties like strength and pliability. This may be due to the chemical nature of the coating and/or to the coating covering or smoothening the relatively rough and porous surface of the textile composed of (multi-filament) polyolefin fibers.

A further advantage of this composite biotextile is that the polyurethane may also function as an adhesive upon a further use of the textile. For example, the composite biotextile may be formed into a multi-layer flat or tubular structure by solvent- or heat-activated binding two or more layers together. Similarly, one or more composite biotextile layers may be laminated by solvent or heat binding to another fabric, film or article; for example, be attached to a stent frame to form a (partly) covered stent, thus reducing the need for attachment means like clamps or sutures. Thermally binding textiles composed of highly-crystalline fibers, such as UHMWPE, without a coating, by using for example laser welding is difficult without distorting or deteriorating properties of the textile, due to the limited melt-flow behavior of such fibers.

Experimental results demonstrate marked improvements in hemocompatibility, abrasion resistance, and suture retention of present composite biotextile.

In accordance with another aspect, the present disclosure provides a method of making a composite biotextile for use in or as a medical implant component, the method comprising steps of a. Providing a polyolefin fibrous construct made from at least one strand having titer of 2-250 dtex, tensile strength of at least 10 cN/dtex and comprising high molar mass polyolefin fibers;
b. Determining locations on the fibrous construct where a cut may be made for an intended use of the construct;
c. Optionally pretreating the fibrous construct at least at the determined locations of the construct with a high-energy source to activate the surface;
d. Solution coating the fibrous construct at least at the determined locations with a coating composition comprising a biocompatible and biostable polyurethane elastomer comprising a polysiloxane in soft segments and/or having hydrophobic endgroups, and a solvent for the polyurethane; and
e. Removing the solvent from the coated fibrous construct; result in a composite biotextile with polyurethane coating on at least part of the surface of the biotextile, with polyurethane present in an amount of 2.5-90 mass % based on composite biotextile.

Further aspects concern the use of such composite biotextile as a component of an implantable medical device and the use of such composite biotextile or such medical implant component in making an implantable medical device; especially for such uses wherein said component of a medical implant will be in contact with body tissue or fluids, such as in orthopedic applications including tissue reinforcement procedures or cardiovascular implants. Examples of materials for soft tissue reinforcement include meshes for hernia repair, abdominal wall reconstruction or degenerative tissue reinforcement. Cardiovascular implants include devices like a vascular graft, a stent cover, a mesh, or a prosthetic valve like a venous valve or heart valve. In many of such applications suturing is used to connect the implant component to other parts of a device or to surrounding tissue or bone.

Other aspects include such medical devices or implants comprising said composite biotextile or medical implant component.

A skilled person will understand that although the experiments are mainly relating to fabrics based on UHMWPE fibers and certain thermoplastic polyurethanes as coating, the disclosures may similarly apply to flexible fibrous constructs made from other fibers of other olefin polymers, and which constructs are sensitive to edge fraying and suture induced tearing; and also to using other polyurethanes as coating materials; as further indicated in the detailed description.

BRIEF DESCRIPTION OF FIGURES

FIG. 5A) and polyurethane-coated UHMWPE fabrics (Ex8-10; FIG. 5B-D).

DETAILED DESCRIPTION

Figure 1:
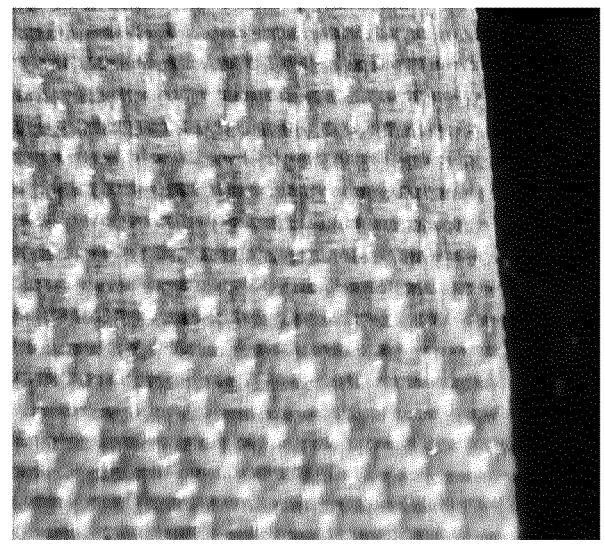
FIG. 1 shows a photo micrograph of the laser-cut edge of UHMWPE fabric, as made with an ultra-short pulsed laser.

Within the context of present disclosures following definitions are used. A fibrous construct is understood to comprise a structure made by interconnecting one or more strands of fibers, for example by interlacing, by using an adhesive or binder, or by partial melting; like a rope, cable, tape or textile. Ropes, cables and tapes are elongated constructs based on strands or fibers. A textile is a flexible material comprising a network of fibers, and typically has a thickness much smaller than its width and length, like a flat sheet having two sides or surfaces, or a hollow tubular form with inner and outer surfaces. Textiles include non-wovens, like a felt of randomly oriented fibers or a unidirectional sheet, and fabrics, like structures made from strands of fibers by techniques like knitting, crocheting, weaving, or braiding. A textile may be isotropic, that is have similar physical or mechanical properties in different directions; be anisotropic as a result of differences in type, number, and/or orientation of fibers; and may have a substantially constant thickness or show variations therein. A strand refers to a bundle of fibers. Fiber(s) is a general term referring to one or more slender (thin and long) threadlike structures; and encompasses continuous fibers (also called filaments) and/or short fibers (also called staple fibers) and may refer to a single fiber or filament and/or to a yarn. A filament is understood to be a (single) thin thread with a generally round or oblong cross-section with diameter generally below 50 µm and typically made by a (melt or solution) spinning process. A yarn is a continuous bundle of filaments and/or staple fibers, optionally twisted together to enhance yarn coherency. A multi-filament yarn is a bundle of filaments, like at least 5 filaments optionally twisted together to enhance yarn bundle coherency. A spun yarn is a thread made by twisting together staple fibers.

A composite fibrous construct, like a composite fabric, refers to a construct that combines two or more structural elements; such as a woven fabric and another fibrous construct (like a cable, a tape, or another fabric) and/or a polymer composition (e.g. as a laminated or coated layer). A laminated textile is a textile having a layer of a polymer attached to one or two sides, which layer may have been applied by heat- or adhesive-bonding a polymer film or sheet, whereas a coated textile has a coating layer (e.g. of a polymer) on one or two sides or on a part thereof, which coating may have been applied as a solution, dispersion or melt, and which may have partially penetrated between or covered fibers of the textile.

A knitted or crocheted fibrous construct is made from at least one strand that is interconnected by looping around itself. A woven fibrous construct is made from at least 2 strands, with a—warp—strand running along the length of the construct and another—weft or fill—strand substantially perpendicular thereto; with warp and weft strands interlacing (crossing over and under each other) in a certain weave pattern. A braided fibrous construct is made from at least 3 strands interlacing one another in a diagonally overlapping pattern; and is typically a flat or a tubular construct of relatively narrow width. Non-woven fibrous constructs can be made from staple or continuous fibers bound together by chemical, mechanical, solvent and/or heat treatment(s); like a felt, or a spun-bound or needle-punched fiber web. The fibers may be randomly oriented such as in a felt but may also be substantially oriented in one (or more) directions. In the last case, and especially if bound together by laminating, coating or impregnating with a polymer, such construct may also be referred to as a unidirectional (UD) composite.

A biocompatible material is biologically compatible by not producing a toxic, injurious, or immunologic response when in contact with living tissue. Biodegradable means a material is susceptible to chemical degradation or decomposition into simpler components by biological means, such as by an enzymatic action. Biostable or bioinert means the material is substantially non-biodegradable under conditions and time of intended use.

In accordance with an aspect, the invention provides a medical implant component comprising a composite biotextile, which composite biotextile comprises A polyolefin fibrous construct comprising at least one strand with titer of 2-250 dtex, tensile strength of at least 10 cN/dtex and comprising high molar mass polyolefin fibers; and A coating comprising a biocompatible and biostable polyurethane elastomer comprising a polysiloxane in soft segments and/or having hydrophobic endgroups; and wherein the polyurethane coating has been applied to at least part of the surface of the fibrous construct, and is present in an amount of 2.5-90 mass % based on composite biotextile.

In another aspect, the invention provides a composite polyurethane/polyolefin biotextile, as defined in the above paragraph, for use as a medical implant component.

The medical implant component comprises or is based on the composite biotextile, meaning that the biotextile forms a structural or strength providing part of the component, or preferably the composite biotextile forms the medical implant component. Examples of other items that may form part of the implant component include a metallic or polymeric stent frame as in case of cardiovascular implants like stent-grafts, or high-strength sutures, suture anchors, plates and screws, or other fixation structures in the case of orthopedic implants. Such implants may be covered with a temporary protective compound or film for packaging, or may be compressed and crimped in a capsule, all of which parts can be removed before using the implant component. Such implant components may also interact with an auxiliary part of the medical device that can serve as a tool in using the implant component to make an actual medical implant; such as a percutaneous delivery system, an introducer sheath, suture passing devices, etc.

In embodiments of present invention, the medical implant component substantially consists or consists of the composite polyurethane/polyolefin biotextile, and does not comprise further parts, which simplifies use of the implant component in making an implant and reduces risk of introducing less or non-desirable parts or compounds.

In embodiments, the polyolefin fibrous construct in the biotextile can be a rope, cable, tape or textile, or a combination thereof; depending on the use conditions for the implant component.

In further embodiments, the polyolefin construct comprises, or consists of a polyolefin textile; like a non-woven or, preferably, a fabric, which can have been made with different forming techniques, like knitting, weaving or braiding. The fabric may be substantially isotropic or may show some anisotropy. The skilled person knows such fabric forming methods and the different characteristics of such fabrics; and will be able to select a suitable type given a specific intended application of the fabric and its requirements. A knitted fabric, for example, has typically a more open structure than a woven fabric and may be easier to deform and extend. A specific advantage of a knitted fabric may be that e.g. extensibility may be different in different directions. Such anisotropic property may for example be useful in designing a component for a vascular device; like a graft or leaflet of a prosthetic valve. A woven structure has the advantage that desired non- or low-stretch properties and certain shape, form or thickness variation can be incorporated into the fibrous construct by applying various weaving techniques, or by using different yarns as warp and weft strands (for example to introduce anisotropy). The skilled person will be able to select a suitable technique and interlacing pattern in combination with selected strands to obtain desired properties, optionally with some routine experiments.

In embodiments of the invention, the polyolefin fibrous construct in the medical component is a woven or knitted fabric, preferably a woven fabric. Typically, woven fabrics with commonly used patterns like plain, twill or basket weave patterns are found to provide good performance. By using different strands as warp versus weft, a woven with anisotropic properties may be formed, reflecting for example typical properties of some natural tissue material, like in leaves of a heart valve. A woven fabric typically has a selvedge (or selvage) at its lengthwise edges, where the weft strands that run perpendicular to the edge of the structure are not extending from the structure as free ends but are continuous at the edge by returning into the woven structure. It will, however, be dependent on the actual use in and design of an implant whether such stable selvedge can remain and function as an edge, or whether a piece of fabric of specific shape needs to be cut from a larger fibrous construct. It is for such latter situations that the present disclosure provides a fibrous construct such as a fabric from which a piece can be cut having stabilized cut edges; that is by a laser cutting step through a polyurethane-coated part of the fibrous construct, as further described hereinafter.

The composite polyurethane/polyolefin biotextile comprises a polyolefin fibrous construct that comprises, or has been made from at least one strand with a titer of 2-250 dtex. The unit dtex or decitex is typically used in fiber industry, like the related unit denier, and indicates the linear density of a strand, fiber, filament or yarn; with 1 dtex being 1 gram per 10.000 meter of strand. The lower the titer, the lower the thickness of a strand. A construct like a fabric made from thin strands will generally be thinner and more flexible or pliable than a construct made from thick strands, although the type of strand and type of polymer in a fiber, as well as type of construct will also have some influence. In embodiments of the invention, the strands have a titer of at most 225, 200, 180, 160, 140, 120, 100, 80, 60 or 50 dtex; and of at least 4, 5, 6, 8, 10, 15, or 20 dtex. In some embodiments, the at least one strand has a titer of 4-140, 6-100 or 8-60 dtex for a good balance between handleability, pliability, low profile, and strength of the construct. The construct, especially a woven fabric, may comprise two or more strands, which may be of the same or different linear density. By using strands of different titer, thickness of the fabric may be varied in length and/or width direction to create local thickness or stiffness differences, or a certain texture, for example with a certain pattern depending on the type of fabric. The skilled person will be able to select strands of suitable titer depending on desired thickness and texture of the fibrous construct.

The composite biotextile comprises a fibrous construct that comprises at least one strand with a titer of 2-250 dtex, tensile strength of at least 10 cN/dtex and comprising high molar mass polyolefin fibers. In embodiments, the construct contains at least 50 mass % of said strands, and the other strands may have different characteristics as long as the construct conforms to the other features as described herein. In preferred embodiments, the fibrous construct contains at least 60, 70, 80, 90, or 95 mass % of said strands, or is made from such strands.

In an embodiment, the polyolefin fibrous construct has a thickness (or diameter) of about 15-300 μm. Thickness of the construct is related to the type of strands, the type of forming technique used in making the construct and its density. Density of a construct, for example areal density of a non-woven or a fabric, depends on the titer of and the distance between strands. Preferably, the polyolefin fibrous construct has a thickness of at most 275, 250, 225, 200, 175, 150, 125, 100, 90, or 80 μm for improved flexibility and pliability, and thickness of at least 20, 25, 30, 35, 40 45, or 50 μm for certain strength and durability properties. These values represent maximum and minimum thickness in case the construct, especially a textile, has not a uniform thickness.

A strand in the polyolefin fibrous construct may be of various different structures and made from different olefinic polymers. In embodiments, the at least one strand of the polyolefin fibrous construct comprises at least one monofilament or multi-filament yarn. In case of a monofilament, a strand is preferably formed by one monofilament, typically with a titer of 2-50 dtex. If the monofilament is thicker, the stiffness of the construct may be too high. Preferably, a monofilament has a titer of at most 45, 40, 35 or 30 dtex for a construct like a fabric with good pliability.

In other embodiments, the at least one strand consists of one or more multi-filament yarns. Given above discussed dimensioning of strands, a multi-filament yarn in the polyolefin fibrous construct can also have a titer of about 2-250 dtex. The yarn preferably has a titer of at most 225, 200, 180, 160, 140, 120, 100, 80, 60 or 50 dtex; and of at least 4, 5, 6, 8, 10, 15, or 20 dtex. In some embodiments, the at least one yarn has a titer of 4-120, 5-80, or 6-60 dtex. In case the strand comprises more than one yarn, titers are chosen to meet indicated ranges for a strand. The multi-filament yarn can be twisted or non-twisted. Twisted yarns generally are easier to handle and convert into a construct, whereas untwisted yarns may result in a more pliable fabric, as filaments may move and shift easier relative to another and the cross-section of a yarn may have become more oblong or flattened in the fabric. In some embodiments, the fibrous construct is made from strands that comprise non-twisted multi-filament yarn, which is advantageous in case of making UD constructs wherein filaments are preferably oriented in parallel. Typically, individual filaments contained in a multi-filament yarn may have a titer per filament that varies widely; like from 0.2 to 5 dtex or preferably 0.3-3 or 0.4-2 dtex per filament, and filaments can have a cross-section that is substantially round but also oblong or any other form.

The polyolefin fibrous construct is made from at least one strand that comprises high molar mass polyolefin fibers. In embodiments, the polyolefin fibers can have been made from one or more polyolefins selected from homopolymers and copolymers, including e.g. biopolymers, terpolymers, etc., containing one or more olefins as monomer units, which polyolefins have a high molar mass and may have been formed by any method known to those skilled in the art. A high molar mass is herein understood to mean a weight averaged molecular weight (or molar mass) of at least 350 kDa, as determined by GPC or as derived from solution viscosity measurements. Suitable examples of polyolefins include polypropylenes, polyethylenes, and their copolymers or blends; like polypropylene homopolymer, medium density polyethylene, linear or high-density polyethylene, copolymers of ethylene and relatively small amounts of one or more alpha-olefins such as butene-1, hexene-1, and octene-1, linear low-density polyethylene, ethylene/propylene copolymers, propylene/ethylene copolymers, polyisoprene and the like. Polypropylene and polyethylene polymers are preferred. An advantage of such high molar mass polyolefin fibers, in addition to their good biocompatibility and biostability, is the relatively high tensile strength such fibers may have; that is a tensile strength of at least 10 cN/dtex, which allows making thin yet strong and durable fibrous constructs.

In further embodiments, the strands in the polyolefin fibrous construct comprise fibers made from a linear polyethylene such as a high molecular weight polyethylene (HMWPE) or an ultra-high molecular weight polyethylene (UHMWPE). The old term 'molecular weight' is still interchangeably used in the art with 'molar mass'; also reflected in the commonly used abbreviation for (ultra-)high molar mass polyethylene.

UHMWPE is a synthetic polymer that shows good biocompatibility in combination with high biostability or bio-inertness, and which has been used in various biomedical devices and implants for quite some time already. UHMWPE is herein understood to be a polyethylene having an intrinsic viscosity (IV) of at least 4 dL/g, like between 4 and 40 dL/g. Intrinsic viscosity is a measure for molar mass that can more easily be determined than actual molar mass parameters like Mn and Mw. IV is determined according to method ASTM D1601(2004) at 135° C. on solution in decalin, the dissolution time being 16 hours, with butylhydroxytoluene as anti-oxidant in an amount of 2 g/L solution, by extrapolating the viscosity as measured at different concentrations to zero concentration. There are various empirical relations between IV and Mw, such relations typically being dependent on factors like molar mass distribution. Based on the equation Mw=$5.37*10^4$ [IV]$^{1.37}$ an IV of 8 dL/g would correspond to Mw of about 930 kDa, see EP0504954A1. In embodiments, the IV of the UHMWPE in the polyolefin film is at least 5, 6, 7 or 8 dL/g and IV is at most 30, 25, 20, 18, 16 or even at most 14 dL/g; to arrive at a balance between high mechanical properties and ease of processing. In general, the IV as measured on the UHMWPE polymer in a fiber or fabric can be somewhat lower than the IV of the polymer as used in making the fibers. During a fiber manufacturing process, like the gel-extrusion method described further on, the polyolefin may be subject to thermal, mechanical and/or chemical degradation, which may result in chain breakage, lowering of the molar mass and/or different molar mass distribution.

In further embodiments of the invention, the UHMWPE in the fibers may be a linear or slightly branched polymer, linear polyethylene being preferred. Linear polyethylene is herein understood to mean polyethylene with less than 1 side chain per 100 carbon atoms, and preferably with less than 1 side chain per 300 carbon atoms; a side chain or branch containing at least 10 carbon atoms. The linear polyethylene may further contain up to 5 mol % of one or more other alkenes that are copolymerizable with ethylene, e.g. $C_3$-$C_{12}$ alkenes like propene, 1-butene, 1-pentene, 4-methylpentene, 1-hexene and/or 1-octene. Side chains and comonomers in UHMWPE may suitably be measured by FTIR; for example on a 2 mm thick compression molded film, by quantifying the absorption at 1375 cm using a calibration curve based on NMR measurements (as in e.g. EP0269151).

The UHMWPE in the fibers may be a single polymer grade, but also a mixture of polyethylene grades that differ in e.g. molar mass (distribution), and/or type and amount of side chains or comonomer(s). The UHMWPE in the fibers may also be a blend with up to 25 mass % of another polyolefin as described above. Generally, the UHMWPE fibers are suitable for medical applications, containing only low amounts of customary and biocompatible additives and residual spin solvent. In embodiments the fibers contain at most 5, 4, 3 2 or 1 mass % of additives. In further embodiments the fibers contain at most 1000 ppm of spin solvent, preferably at most 500, 300, 200, 100 or 60 ppm.

In embodiments, the UHMWPE fibers comprised in strands of the polyolefin fibrous construct have a tensile strength or tenacity of at least 15, 20, 25, 28, 30 cN/dtex and typically of at most about 40 cN/dtex, or at most 37 or 35 cN/dtex; and preferably a tensile modulus of at least 300 and up to 1500 cN/dtex. Tensile strength (or strength or tenacity) and tensile modulus (or modulus) of UHMWPE fibers are defined and determined at room temperature, i.e., about 20° C., for example on multifilament yarn as specified in ASTM D885M, using a nominal gauge length of the fibre of 500 mm, a crosshead speed of 50%/min and Instron 2714 clamps, of type "Fibre Grip D5618C". Based on the measured stress-strain curve the modulus is determined as the gradient between 0.3 and 1% strain. For calculation of the modulus and strength, the tensile forces measured are divided by the titer, as determined by weighing 10 metres of yarn; values in cN/dtex are calculated assuming a density of 0.97 g/cm$^3$.

In embodiments, the strands of the polyolefin fibrous construct comprise at least 80 mass %, or at least 90 mass % of UHMWPE fibers or filaments with a tenacity of at least 15 cN/dtex. In other embodiments strands of the construct, for example the warp and/or the fill threads of a woven structure, substantially consist or consist of UHMWPE fibers or multi-filament yarn. In an embodiment, the warp strands (substantially) consist of UHMWPE and the weft strands (substantially) consist of another polymer like a polyester such as PET, alternatively weft strands consist of UHMWPE and warp strands of PET. Such fabrics may show anisotropic properties, like different strength and/or elongation in warp vs weft direction.

In embodiments, the high molar mass polyolefin fibers comprised in the polyolefin fabric have been made by a so-called gel-spinning process. In a typical gel-spinning process a solution of the polymer in a suitable spin solvent, optionally containing dissolved and/or dispersed further components, is spun and cooled into gel fibers that are subsequently drawn before, during and/or after partially or substantially removing the spin solvent. Gel spinning of a solution of UHMWPE is well known to the skilled person; and is described in numerous publications, including EP0205960A, EP0213208 A1, U.S. Pat. No. 4,413,110, GB2042414 A, EP0200547B1, EP 0472114 B1, WO2001/73173 A1, WO2015/066401A1, in Advanced Fiber Spinning Technology, Ed. T. Nakajima, Woodhead Publ. Ltd (1994), ISBN 1-855-73182-7, and in references cited therein. Examples of suitable UHMWPE multi-filaments yarns include those available as Dyneema Purity® grades (e.g. from DSM Biomedical BV, Sittard-Geleen NL).

In further embodiments, the polyolefin fibrous construct in the biotextile comprises a combination of two or more different constructs; such as a textile and a rope, cable, or tape, or a combination of a polyolefin woven fabric and a rope, cable, tape or non-woven.

The composite biotextile comprises a polyolefin fibrous construct and a coating comprising a biocompatible and biostable polyurethane elastomer having hydrophobic end-groups. An elastomer is a polymeric material showing relatively low Young's modulus, high elongation and elastic recovery after elongation or deformation, when compared with other materials like polyolefins such as polyethylenes and polypropylenes. A thermoplastic elastomer can be repeatedly molten by heating and re-solidified by cooling; and derives its elasticity from reversible physical cross-linking instead of from chemical cross-links as in thermoset elastomers. The polyurethane elastomer component of present composite fabric may be thermoplastic or not; but is soluble in a suitable solvent, the advantage being that a solution of the elastomer of relatively low viscosity can be used to coat, within present context this includes to optionally impregnate, the polyolefin fibrous construct at a temperature well below the melting temperature of the polyolefin, so as to not deteriorate fiber and construct properties by partial melting; considering that the melting point of polyolefin may be below the melting point of a thermoplastic polyurethane elastomer (TPU). Use of a solution of a polyurethane elastomer or a TPU to coat the polyolefin construct also has the advantage that by choosing conditions and solution viscosity a coating layer may be formed predominantly on the surface of the fibrous construct, but a solution may also be made to penetrate between strands and fibers and to partially or even fully cover fibers and impregnate the construct. A coated fibrous construct like a fabric wherein strands or fibers are fully covered or embedded by TPU can also be called an impregnated fabric. Such coated or impregnated fabric may have several properties distinct from the polyolefin fabric, like reduced gas and/or liquid permeabilities, and surface properties may be much like those of the polyurethane. In case only one side of a polyolefin fabric is coated with polyurethane with no or limited penetration between fibers, surface properties of only one side of the fabric will be changed, and the non-coated side may stay substantially unchanged; except for e.g. permeability of the fabric. Such composite biotextile may for example show different interactions with biological matter; for example, the coated side may show good blood compatibility without causing clotting, whereas at the non-coated side having more surface texture and/or porosity ingrowth of tissue may occur when used as a graft material. A coating of polyurethane may be present on all surface of the polyolefin construct, but also only locally at selected parts of the surface, and on one or both sides of the construct; as further discussed hereinafter.

Polyurethane elastomers are typically block copolymers (also called segmented copolymers). Block copolymers are polymers comprising blocks (also called segments) of polymers (including oligomers) that are chemically distinct, and which show different thermal and mechanical properties, and different solubilities. Often the blocks in a block copolymer comprising two (or more) types of blocks are referred to as being 'hard' and 'soft' polymer blocks, such different blocks resulting in microphase separation of hard and soft blocks. The hard block in a block copolymer typically comprises a rigid or high modulus polymer, with a melting temperature ($T_m$) or a glass transition temperature (Tg) higher than the use temperature, of e.g. about 35° C. The soft block in the block copolymer often comprises a flexible, low modulus, amorphous polymer with a $T_9$ lower than 25° C., preferably lower than 0° C. Thermal parameters like $T_m$ and $T_9$ are generally determined on dry samples; using well-known techniques like DSC or DMA. In such phase-separated block copolymers, the hard segments function as physical crosslinks for the flexible soft segments, resulting in materials having properties ranging from fairly stiff to flexible and elastic, depending on the ratio of hard to soft blocks. Depending on type and amount of hard blocks, the polyurethane may show good stability and elasticity over a desired temperature range without the need for chemical crosslinking; and can generally be processed as a thermoplastic. The term thermoplastic polyurethane elastomer basically denotes a family of polymers with a backbone comprising the reaction product of at least three principle components; that are a diisocyanate, a diol chain extender and a polymer diol or macroglycol, and optionally a monofunctional compound as chain stopper forming endgroups. The backbone of the polyurethane elastomer or the TPU applied in present invention is typically linear and has one or two endgroups, preferably one or two hydrophobic endgroups.

In embodiments, the polyurethane elastomer comprises hard blocks that include urethane groups and optionally urea groups in repeating units, which have resulted from reaction of a diisocyanate with a diol and optionally a diamine as chain extender.

Suitable diisocyanates include aromatic, aliphatic and cycloaliphatic compounds, having an average of 1.9-2.1 isocyanate groups per molecule. In an embodiment, the diisocyanate comprises 4,4'-diphenylmethane diisocyanate (MDI), 2,4-toluene diisocyanate, 2,6-toluene diisocyanate (TDI), 1,4-phenylene diisocyanate, hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof. In an embodiment, the diisocyanate comprises hexamethylene diisocyanate, dicyclohexylmethane 4,4'-diisocyanate, isophorone diisocyanate, or a mixture thereof. In an embodiment, the diisocyanate consists of hexamethylene diisocyanate, dicyclohexylmethane 4,4'-diisocyanate, isophorone diisocyanate, or a mixture thereof. In an embodiment, the diisocyanate comprises 4,4'-diphenylmethane diisocyanate, 2,4-toluene diisocyanate, 2,6-toluene diisocyanate, or 1,4-phenylene diisocyanate. In an embodiment, the diisocyanate consists of 4,4'-diphenylmethane diisocyanate, 2,4-toluene diisocyanate, 2,6-toluene diisocyanate, 1,4-phenylene diisocyanate, or a mixture thereof.

In an embodiment, the molar mass of the diisocyanate is from 100 to 500 g/mol. In an embodiment, the molar mass of the diisocyanate is from 150 to 260 g/mol.

Chain extenders are typically low molar mass aliphatic compounds, having two or more hydroxyl or amine groups. Bifunctional chain extenders result in linear, generally thermoplastic polymers, whereas multifunctional isocyanates and/or chain extenders would lead to branched or crosslinked products. In an embodiment, the bifunctional chain extender has a molar mass of at least 60 g/mol, at least 70 g/mol, at least 80 g/mol, at least 90 g/mol, or at least 100 g/mol. In an embodiment, the chain extender has a molar mass of at most 500 g/mol, at most from 400 g/mol, at most 300 g/mol, at most 200 g/mol, or at most 150 g/mol. In an embodiment, the chain extender comprises ethylene glycol, diethylene glycol, propylene glycol, dipropylene glycol, 1,3-propanediol, 1,4-butanediol, 1,5-pentanediol, 1,6-hexanediol, or 1,8-octanediol; and/or such corresponding diamines. In embodiments, the polyurethane elastomer comprises only diol chain extenders and shows thermoplastic behavior; that is the polyurethane elastomer is a thermoplastic polyurethane elastomer or TPU.

In other embodiments, the polyurethane elastomer comprises hard blocks having both urethane and urea linkages. The advantage thereof is enhanced interaction between the hard blocks, allowing a higher content of soft blocks resulting in block copolymers showing enhanced flexibility and elasticity, and excellent flex life or fatigue resistance. Depending on the ratio diol/diamine, the polyurethane elastomer may show such strong interaction that at a melt processing temperature thermal degradation may be such that solution processing is to be preferred for optimal performance. Commercially available examples of such polyurethane elastomers comprising both urethane and urea linkages include Biospan® products (available from e.g. DSM Biomedical BV, Sittard-Geleen NL).

In further embodiments, the polyurethane elastomer comprises soft blocks derived from at least one aliphatic polymer diol or polyol, which is chosen from the group consisting of polyethers, polyesters, polyacrylates, polyolefins and polysiloxanes (also called silicones); which polymers are bifunctional with hydroxyl (or amine) terminal groups. Such polymer diols for the soft blocks are understood herein to include oligomers, homopolymers and copolymers, and polyesters are considered to include polycarbonates. Generally known polyurethane block copolymers and methods to prepare these copolymers are described in a.o. U.S. Pat. Nos. 4,739,013, 4,810,749, 5,133,742 and 5,229,431.

In embodiments of the present disclosure the polyurethane elastomer comprises as soft block at least one polymer diol chosen from an aliphatic polyester diol, an aliphatic polyether diol, a poly(isobutylene) diol and a polysiloxane diol. As for chain extenders, also amine-functional soft blocks can be used, resulting in additional urea linkages. Biocompatibility and biostability of such polyurethane block copolymers in the human body has been proven.

Mechanical and other properties of a polyurethane block copolymer can be tailored by varying chemical compositions and/or molar mass of the blocks. The hard blocks of a polyurethane elastomer for use in the invention may have a molar mass of about 160 to 10,000 Da, and more preferably of about 200 to 2,000 Da. The molar mass of the soft segments may be typically about 200 to 100,000 Da, and preferably at least about 400, 600, 800 or 1000 Da and at most about 10,000, 7500, 5000, 4000, 3000 or 2500 Da. Within the context of present disclosure, molar mass of polymers and oligomers discussed refers to the number average molar mass ($M_n$), as for example derived from GPC measurements. The ratio of soft to hard blocks can be chosen to result in certain stiffness or hardness of the polymer. Typically, hardness of the polyurethane as measured with the Shore durometer hardness test using A or D scales, may be from 40 ShA, or at least 50 or 60 ShA and up to 80, 75, 70, 65 or 60 ShD or up to 100, 90 or 85 ShA, generally representing a flexural modulus range of about 10 to 2000 MPa. In embodiments, the polyurethane elastomer has a hardness from 40 ShA to 60 ShD, preferably 40-100 ShA or 40-90 ShA.

In further embodiments of present invention, the polyurethane elastomer comprises an aliphatic polyether or an aliphatic polyester as soft block, more specifically an aliphatic polycarbonate. Suitable aliphatic polyethers include poly(propylene oxide) diols, poly(tetramethylene oxide) diols, and their copolymers. Suitable aliphatic polyesters are generally made from at least one aliphatic dicarboxylic acid and at least one aliphatic diol, which components are preferably chosen such that an essentially amorphous oligomer or polymer is formed having a $T_9$ below 10, 0, or −10° C. Aliphatic polycarbonate diols are based on similar aliphatic diols as used for polyester diols, and can be synthesized via different routes as known in the art. Suitable examples include poly(hexamethylene carbonate) diols and poly(polytetrahydrofuran carbonate) diols. In an embodiment, the soft block is based on a poly(hexamethylene carbonate) diol, a poly(polytetrahydrofuran carbonate) diol, or a mixture thereof. In case the soft blocks of the polyurethane substantially consist of such polyols and contain no polysiloxane, the polymer has at least one hydrophobic endgroup, and preferably two hydrophobic endgroups.

In a further embodiment, the soft block comprises a polysiloxane diol such as a poly(dimethyl siloxane) diol, a polycarbonate diol, or a poly(tetramethylene oxide) diol. In an embodiment, the soft block is based on a polysiloxane diol, a polycarbonate diol, a poly(tetramethylene oxide) diol, or a mixture thereof. In an embodiment, the soft block comprises a mixture of two or more of a polysiloxane diol, a polycarbonate diol, or a poly(tetramethylene oxide) diol. In an embodiment, the soft block is based on a mixture of two or more of a polysiloxane diol, a polycarbonate diol, or a poly(tetramethylene oxide) diol. In an embodiment, the soft block comprises a polysiloxane diol and one or more of a polycarbonate diol and a poly(tetramethylene oxide) diol. In an embodiment, the soft block is based on a polysiloxane diol and one or more of a polycarbonate diol and a poly(tetramethylene oxide) diol.

In an embodiment, the soft blocks or the polymer diol may further comprise a $C_2$-$C_{16}$ fluoroalkyl diol or $C_2$-$C_{16}$ fluoroalkyl ether diol. In an embodiment, the soft block in the polyurethane backbone comprises the residue of 1H,1H,4H,4H-Perfluoro-1,4-butanediol, 1H,1H,5H,5H-Perfluoro-1,5-pentanediol, 1H,1H,6H,6H-perfluoro-1,6-hexanediol, 1H,1H,8H,8H-Perfluoro-1,8-octanediol, 1H,1H,9H,9H-Perfluoro-1,9-nonanediol, 1H,1H,10H,10H-Perfluoro-1,10-decanediol, 1H,1H,12H,12H-Perfluoro-1,12-dodecanediol, 1H,1H,8H,8H-Perfluoro-3,6-dioxaoctan-1,8-diol, 1H,1H,11H,11H-Perfluoro-3,6,9-trioxaundecan-1,11-diol, fluorinated triethylene glycol, or fluorinated tetraethylene glycol.

In an embodiment, the $C_2$-$C_{16}$ fluoroalkyl diol or $C_2$-$C_{16}$ fluoroalkyl ether diol has an $M_n$ of at least 150 g/mol, at least 250 g/mol, or at least 500 g/mol. In an embodiment, the fluoroalkyl diol or fluoroalkyl ether diol has a molar mass of at most 1500 g/mol, at most 1000 g/mol, or at most 850 g/mol. In an embodiment, the $C_2$-$C_{16}$ fluoroalkyl diol or $C_2$-$C_{16}$ fluoroalkyl ether diol is present in an amount of at least 1 mass %, at least 2 mass %, or at least 5 mass %, based on the total mass of the polyurethane. In an embodiment, the $C_2$-$C_{16}$ fluoroalkyl diol or $C_2$-$C_{16}$ fluoroalkyl ether diol is present in an amount of at most 15 mass %, at most 10 mass %, or at most 8 mass %, based on the total mass of the polyurethane.

The polyurethane elastomer may comprise one or more hydrophobic endgroups. An endgroup is a generally a non-reactive moiety present at a terminal end of a molecule. In an embodiment, the polyurethane elastomer is linear and comprises a hydrophobic endgroup at one end or terminus, preferably at each terminus of the backbone; that is an average of about 2 endgroups. In an embodiment, the hydrophobic endgroup is a linear compound. In another embodiment, the hydrophobic endgroup is branched. An endgroup may have been formed by reacting a terminal isocyanate group present during or after forming the polymer backbone with a co-reactive group on a monofunctional compound or chain stopper. For instance, a formulation for forming a polyurethane may comprise a diisocyanate, a polymeric aliphatic diol, a chain extender, and a monofunctional compound; like 1-octanol or octylamine to form a C alkyl endgroup.

In an embodiment, the hydrophobic endgroup comprises a $C_2$-$C_{20}$ alkyl, a $C_2$-$C_{16}$ fluoroalkyl, a $C_2$-$C_{16}$ fluoroalkyl ether, a hydrophobic poly(alkylene oxide) or a polysiloxane, including copolymers thereof. In an embodiment, the hydrophobic poly(alkylene oxide) is poly(propylene oxide), poly(tetramethylene oxide) or a copolymer thereof. In an embodiment, the hydrophobic endgroup is a polysiloxane, like a poly(dimethyl siloxane). In an embodiment, the endgroup comprises $C_2$-$C_{20}$ alkyl, $C_2$-$C_{16}$ fluoroalkyl, $C_2$-$C_{16}$ fluoroalkyl ether, or a hydrophobic poly(alkylene oxide). Such endgroups may be formed with monofunctional alcohols, including carbinols, or amines of the foregoing. Such polyurethane elastomers having hydrophobic endgroups are found to positively affect properties of the polyurethane and its interaction with other materials, including other polymers like polyolefins and bodily tissue and fluid like blood.

In an embodiment, the hydrophobic endgroup comprises $C_2$-$C_{16}$ fluoroalkyl or $C_2$-$C_{16}$ fluoroalkyl ether. Such endgroups may be formed with monofunctional alcohols or amines comprising $C_2$-$C_{16}$ fluoroalkyl or $C_2$-$C_{16}$ fluoroalkyl ether. In an embodiment, the endgroup is formed from 1H,1H-Perfluoro-3,6-dioxaheptan-1-ol, 1H,1H-Nonafluoro-1-pentanol, 1H,1H-Perfluoro-1-hexyl alcohol, 1H,1H-Perfluoro-3,6,9-trioxadecan-1-ol, 1H,1H-Perfluoro-1-heptyl alcohol, 1H,1H-Perfluoro-3,6-dioxadecan-1-ol, 1H,1H-Perfluoro-1-octyl alcohol, 1H,1H-Perfluoro-1-nonyl alcohol, 1H,1H-Perfluoro-3,6,9-trioxatridecan-1-ol, 1H,1H-Perfluoro-1-decyl alcohol, 1H,1H-Perfluoro-1-undecyl alcohol, 1H,1H-Perfluoro-1-lauryl alcohol, 1H,1H-Perfluoro-1-myristyl alcohol, or 1H,1H-Perfluoro-1-palmityl alcohol.

In an embodiment, the hydrophobic endgroup is monomeric and has a molar mass of 200 g/mol or more, 300 g/mol or more, or 500 g/mol or more; and of 1,000 g/mol or less or 800 g/mol or less. In an embodiment, the endgroup is polymeric and has a molar mass of 10,000 g/mol or less, 8,000 g/mol or less, 6,000 g/mol or less, or 4,000 g/mol or less. In an embodiment, the endgroup is polymeric and has a molar mass of 500 g/mol or more, 1,000 g/mol or more, or 2,000 g/mol or more.

In an embodiment, the hydrophobic endgroup is present in an amount of at least 0.1 mass %, at least 0.2 mass %, at least 0.3 mass %, or at least 0.5 mass %, based on the total mass of the polyurethane. In an embodiment, the hydrophobic endgroup is present in an amount of at most 4 mass %, at most 3 mass %, at most 2 mass % or at most 1 mass %, based on the total mass of the polyurethane. In an embodiment, the hydrophobic endgroup is present in an amount of at least 0.1 mass %, at least 0.2 mass %, at least 0.3 mass %, or at least 0.5 mass %; and in an amount of at most 4 mass %, at most 3 mass %, at most 2 mass % or at most 1 mass %, based on the total mass of the polyurethane.

The hard blocks in such polyurethane or TPU are typically based on an aromatic diisocyanate like toluene diisocyanate (TDI) or methylenediphenyl diisocyanate (MDI), and a low molar mass aliphatic diol like 1,4-butanediol. Polyether and polycarbonate polyurethanes may be suitably used for biomedical applications, in view of their flexibility, strength, biostability, biocompatibility and wear resistance. A TPU containing a combination of a polyether and a polysiloxane or a polycarbonate and a polysiloxane, for example as the soft blocks, shows a unique combination of properties and may advantageously be used as the polyurethane in the coating. Commercially available examples of such polymers include Carbosil® TSPCU products (available from DSM Biomedical BV, Sittard-Geleen NL).

In a further embodiment, the polyurethane or TPU may be a blend of two or more polymers. In other embodiments the polyurethane or TPU may comprise one or more customary additives that are allowed for the targeted use of the composite biotextile; in addition to e.g. catalyst residues. Examples of additives include stabilizers, anti-oxidants, processing aids, lubricants, surfactants, antistatic agents, colorants, radiopacifiers and fillers. The additives may be present in the typically effective amounts as known in the art, such as 0.01-5 mass % based on the amount of the polyurethane, preferably 0.01-1 mass %. In another embodiment, the polyurethane or TPU substantially consists of polymer, and is substantially free of additives.

In a further embodiment the polyurethane coating comprises a radiopacifier as additive, typically at a relatively high amount like 15-80 mass % for effective visualization in medical imaging techniques using x-rays or other radiation. In an embodiment, the radiopacifier comprises tantalum, gold, platinum, tungsten, iridium, platinum-tungsten, platinum-iridium, palladium, rhodium, barium sulfate, bismuth subcarbonate, bismuth oxychloride, bismuth trioxide, ionic or non-ionic contrasting agents such as diatrizoates, iodipamide, iohexyl, iopamidol, iothalamate, ioversol, ioxaglate, and metrizamide, or a combination thereof. In an embodiment, the radiopacifier comprises tantalum, gold, platinum, tungsten, or a mixture or alloy thereof. In an embodiment, the radiopacifier is present as particles. In an embodiment, the radiopacifier particles have an average particle diameter of at least 1 nm, preferably at least 5, 10, 25, 50, 100, or 200 nm. In an embodiment, the radiopacifier particles have an average particle diameter of at most 3 µm, preferably at most 2, 1, 0.5, or 0.2 µm. Average particle diameter is measured using photon correlation spectroscopy (PCS) in accordance with ISO13321:1996. In an embodiment, the radiopacifier is surface treated with an adhesion promoter to enhance adhesion to the polyurethane; like with a glycidyl methacrylate (GMA) modified random ethylene/acrylate copolymer, or a GMA and maleic anhydride (MA) modified random ethylene/acrylate copolymer. In an embodiment, the radiopacifier is present in the polyurethane in an amount of at least 20, 30, 40, or 50 mass %; and of at most 75, 70, 65, 60 or 55 mass % based on polyurethane.

In embodiments wherein the composite biotextile comprises a polyolefin fibrous construct and a coating comprising a biocompatible and biostable thermoplastic polyurethane elastomer (TPU), the TPU may show at a temperature above its melting point a melt flow that is at least 10 times higher than the melt flow of the polyolefin. A TPU generally will have a melting point that is higher than the melting point of the polyolefin, which polyolefin may melt in a range 130-190° C. (a.o. depending on amount of oriented crystals present; for example in high-strength UHMWPE fibers, which show multiple melting in a range 130-155° C.). Basically, this melt flow feature specifies that the melt viscosity of the polyolefin at a certain temperature above the melting points of polyolefin and of TPU, for example at a temperature that is locally increased upon laser cutting as illustrated below, is significantly higher than the melt viscosity of the TPU, such that molten polyolefin shows substantially no melt flow whereas the molten TPU may flow into the fibrous construct or around fibers of the construct. Melt flow is typically measured as melt flow rate (MFR; also called melt flow index, MFI) following ASTM D1238 standard and reported as the amount of polymer extruded during a fixed while (that is in g/10 min) from a certain opening under a certain weight and at a certain temperature as specified for different polymers in the standard. High molar mass polyolefins, like HMWPE, typically have such high melt viscosity that a high mass is used in the test (21.6 kg vs 2.16 kg for most polymers) to have a measurable result (e.g. 0.2-1 g/10 min at 190° C. and 21.6 kg). UHMWPE grades typically have such high viscosity that there is no measurable melt flow under such conditions. In embodiments, the TPU has at said temperature above its melting point, for example at 210-240° C., a melt flow rate that is at least 10, 20, 40, 60 or even 100 times the melt flow rate of the polyolefin, like a UHMWPE.

The composite biotextile comprises a polyolefin fibrous construct and a coating comprising a biocompatible and biostable polyurethane elastomer, wherein the polyurethane coating has been applied to and is present on at least part of the surface of the construct, and in case of a textile or fabric on at least part of the surface of at least one side thereof. In embodiments, the polyurethane coating is present on substantially all surface area of the fibrous construct, like on both sides of a polyolefin fabric. Such composite biotextile can for example have been made by dip-coating the polyolefin construct by immersing in a solution of the polyurethane and subsequently removing the solvent. The thickness of the coating layer can be adjusted by varying the concentration of polyurethane in the solution or by varying the pick-up speed of removing the fibrous construct from the solution. Depending on said conditions and on the thickness and packing density of strands in the construct, that is on how much space there is available as e.g. pores between strands and individual fibers in the construct, the polyurethane can be present merely as a surface coating or may have impregnated or embedded the fibrous construct as well. In such latter case, the composite biotextile could also be referred to as a fiber-reinforced polyurethane. Anyhow, such fully coated composite biotextile will show several different properties compared to the non-coated polyolefin construct, depending on the type and amount of polyurethane coating. An advantage of such composite biotextile is that it can be cut using a laser at any location on the composite biotextile, to make a piece of material of desired shape and having a stabilized cut edge showing enhanced fraying resistance and suture retention strength versus the non-coated fibrous construct. A suitable laser for such purpose is selected and applied with such settings that enough energy is provided at the location to make cut through the composite biotextile, whereby optionally a local cutting temperature may be reached that is above the melting point of the polyurethane, especially a TPU; such that the TPU locally may form a melt that flows to connect cut fiber ends with each other and/or with other fibers in the biotextile. The laser cut itself is likely resulting from very local heating of fibers and coating to such temperature that material degrades and evaporates by the focused laser energy. Therefore, laser settings are selected such that no excessive heating occurs, to prevent forming of an irregular and deformed or disrupted edge zone adjacent to the cut in the biotextile. An overheated edge may also show undesirable stiffening at the edge zone, deteriorating pliability of the biotextile. The skilled person will be able to select a laser suitable for said purpose, like a $CO_2$, Nd or Nd-YAG laser, and to select proper settings including controlling the energy of the beam by e.g. pulsing. Generally, a $CO_2$ laser can be suitably used for cutting the composite biotextile. It has been observed, however, that when using a continuous wave laser excessive heat-transfer in the composite biotextile may occur, thereby distorting the cut edge or causing partial melting or shrinkage of the polyolefin (like UHMWPE) construct due to e.g. thermal relaxation effects. In embodiments of the invention, a pulsed laser is applied; that is a laser that emits light not in a continuous mode, but rather in the form of optical pulses. Therefore, in embodiments short pulse or ultra-short pulse lasers, like nano-, pico-, or femtosecond pulsed lasers, are applied as they do not excessively heat the composite biotextile to cause morphological distortion, while polyurethane may still melt to secure the cut edge.

In other embodiments, the polyurethane elastomer coating has been applied to and is present on part of the surface area of the fibrous construct, like on (corresponding) parts of the surface area of both sides of a polyolefin textile. The polyurethane can for example be applied as one or more stripes, that is as an elongated coated and/or impregnated area or section of the fibrous construct like a fabric with a width of at most 10 mm. Such stripe may for example have been formed from an array of adjacently or partly overlapping applied polyurethane solution droplets; such as by using a (micro-) pipette, spray coating or an ink jet printing device. The polyurethane solution may for example have been applied to both sides of a fabric at opposing and corresponding places, or at one side only; to basically surface coat the fabric, or to partially impregnate the fabric like in case of a fabric into which the applied solution will easily penetrate into the fabric across its thickness. A stripe can also result, especially if merely a stripe at an edge zone of the construct is desired, from a dip-coating process wherein the construct is only partly submerged in polyurethane solution at one or more of its edges. In embodiments, the stripes of polyurethane coating have a width of at most 8, 6, 5, or 4 mm. Minimum width of stripe may be as small as 1 mm, or at least 2 or 3 mm for effectively increasing suture retention and/or fraying resistance. The stripes are at least positioned on those places or areas of the construct, where during an intended use of the biotextile a (laser) cut is to be made to further size and shape the composite biotextile. Polyurethane coating may also be applied at locations of the fibrous construct to change other properties of the construct. The skilled person will be able to identify such locations, for example while reviewing performance requirements of an intended use of the construct; by reviewing literature, by computer aided designing and modelling, or by failure analysis on existing devices and/or performing tests on prototypes.

In further embodiments, the polyurethane coating is present on part of the surface of one side of the composite biotextile. Stripes of polyurethane can have been applied to the polyolefin construct using spray coating or ink jet coating, similarly as described above. In other embodiments, the polyurethane coating is present on substantially all surface area of one side of the composite biotextile. A one-side polyurethane-coated composite biotextile, for example a relatively dense fabric that was coated by using solvent casting, spray or inkjet coating, may be advantageously used in biomedical applications wherein a relatively smooth coated surface of the biotextile is in contact with blood and the non-coated surface faces tissue; for example as a stent-graft material combining good blood compatibility with tissue in-growth, and showing suitable suture retention strength.

In still further embodiments, the polyurethane coating is present on part of the surface area of one side and on substantially all surface area of the other side of the composite biotextile.

The composite biotextile comprises a polyolefin fibrous construct and a coating comprising a biocompatible and biostable polyurethane elastomer, wherein the polyurethane is present in an amount of 2.5-90 mass % of the composite biotextile. Such amount will depend a.o. on the relative surface area of the fibrous construct that is coated (and optionally impregnated). In embodiments, polyurethane is present in an amount of at least 5, 10, 15, 20 or 25 mass %, and of at most 80, 70, 60, 50, 40 or 30 mass %. Lower amounts of polyurethane coating relate typically to a composite biotextile that is partially coated on one side, the higher ranges relate to substantially fully, and two-sided, coated composite biotextiles.

In other embodiments, the amount of polyurethane in the composite biotextile may be expressed in the amount per surface area or areal density; such as an amount of 0.2-10 mg/cm$^2$ based on composite biotextile, or at least 0.5, 1.0, 1.5, 2.0 or 2.5 mg/cm$^2$ and at most 9, 8, 7, 6, or 5 mg/cm$^2$, depending on factors as discussed above.

In an embodiment, the composite biotextile has a cross-section of 15-350 μm or a thickness of about 15-350 μm. Thickness (or cross-section) of the composite biotextile is related to the type of strands, the type of forming technique used in making the polyolefin fibrous construct and density of the polyolefin construct; and further related to the amount of polyurethane, and whether polyurethane is only on the surface and/or between strands in the composite biotextile. In embodiments, the composite biotextile is a coated textile with a thickness of at most 325, 300, 275, 250, 225, 200, 175, 150, 125, 100, 90, or 80 μm for improved flexibility and pliability, and thickness of at least 20, 25, 30, 35, 40 45, or 50 μm for certain strength and durability properties.

In further embodiments, the invention provides a piece of composite biotextile as described above, which has a cut edge that is coated (and/or impregnated) with polyurethane elastomer, i.e. the biotextile has a stable or stabilized cut edge which is not a (woven) selvage. In other words, the composite biotextile has at least one cut edge that is coated and/or impregnated with the polyurethane. Such cut edge typically is the result of cutting a composite biotextile of the invention with a (pulsed) laser at a location where polyurethane coating is present, as described in the above.

In an embodiment, the composite biotextile, like a fabric, has a cut edge and a suture retention strength at the cut edge of at least 15 N, as measured with the method described in the experiments. In further embodiments, the composite biotextile has such suture retention strength of at least 20, 22 or 24 N; whereas such strength may be at most about 50, 45 or 40 N.

In accordance with another aspect, the present disclosure provides a method of making a composite biotextile for use in or as a medical implant component, the method comprising steps of a. Providing a polyolefin fibrous construct comprising at least one strand having titer of 2-250 dtex, tensile strength of at least 10 cN/dtex and comprising high molar mass polyolefin fibers;

b. Determining locations on the fibrous construct where a cut may be made for an intended use of the construct;

c. Optionally pretreating the fibrous construct at least at the determined locations with a high-energy source to activate the surface;

d. Solution coating the fibrous construct at least at the determined locations with a coating composition comprising a biocompatible and biostable polyurethane elastomer comprising polysiloxane in soft segments and/or having hydrophobic endgroups and a solvent for the polyurethane; and e. Removing the solvent from the coated fibrous construct;

result in a composite biotextile with polyurethane coating on at least part of the surface of the biotextile, with polyurethane present in an amount of 2.5-90 mass % based on the composite biotextile.

In embodiments of this method, the fibrous construct, the polyurethane elastomer, and the steps may further include the various features and embodiments as already described hereinabove, and which features may be present in any combination, unless a skilled person likely finds such combination technically not feasible.

The method of present disclosure comprises a step of providing a polyolefin fibrous construct comprising, or substantially made from, at least one strand having a titer of 2-250 dtex, tensile strength of at least 10 cN/dtex and comprising high molar mass polyolefin fibers, including the various optional or preferred embodiments as described hereinabove for the polyolefin fibrous construct.

The next step of the method is determining locations on the fibrous construct where a cut may have to be made or will be made to size or shape the construct for an intended use; which cutting can result in a non-stabilized edge, for example when made in a polyolefin fabric, and which cut edge would likely show fraying or raveling during subsequent use or when a suture would be placed through the fabric near an edge and tensioned. In embodiments of the method, the skilled person may identify such locations on the construct for example as part of development of the construct for its intended use in or as a component of a medical device; which will depend on the design of the component and/or the device, like a catheter balloon, vascular graft, stent-graft, occlusion device or prosthetic heart valve skirt or leaflet.

The method of present disclosure optionally comprises a step of pretreating the fibrous construct at least at the determined locations with a high-energy source to activate the surface for improved bonding to polyurethane, while simultaneously cleaning the surface. In case of a textile with two opposite surfaces, pretreating may be done at least at the determined locations on at least one side of the textile, but also on both sides at opposing and corresponding locations; depending of the type textile and penetration depth of the pretreatment. Polyolefin fibers have a non-polar and non-reactive surface, to which more polar polymers like polyurethanes may show little adhesion. Surface activation by for example a plasma or corona treatment is known, and may introduce functional groups, for example oxygen-containing groups; which may increase adhesion of polyurethane. Suitable examples of plasma surface treatments include cold plasma treatments, which can be performed at atmospheric or reduced pressure and at a temperature that does not negatively affect the polyolefin construct, for example with oxygen being present. In an embodiment, the pretreatment step comprises atmospheric plasma activation. In an embodiment, the pretreatment step is performed to activate all surface of the polyolefin fibrous construct. The inventors observed that the combination of surface pretreatment and using a polyurethane, which has polysiloxane in soft segments and/or hydrophobic endgroups, as coating polymer contributes to the favorable performance and durability of the composite biotextile thus made.

The method of present disclosure further comprises a step of solution coating the fibrous construct at least at the determined, and optionally pretreated locations with a coating composition comprising a biocompatible and biostable polyurethane, a solvent for the TPU, and optionally auxiliary compounds. Suitable polyurethanes for use in this method are those as described above for the composite biotextile, including the compositions, characteristics and various optional or preferred embodiments. Polyurethanes typically may absorb moisture from the environment like up to several mass %, and are preferably dried before dissolving in solvent, e.g. to a level of less than 0.05 mass % of water. Solution coating is well known to a skilled person, and can be performed using various application techniques, like using a pipette or a syringe, dip-coating, spray coating, ink jet application, and the like; from which the skilled person can select the method most suitable for an actual situation based on common knowledge and some routine testing. The polyolefin fibrous construct may be partially coated, to form one or more stripes or any other pattern, or fully coated and impregnated as discussed above. The solution may be applied in one step, but also in multiple steps applying e.g. smaller amounts, for example with certain time between steps to allow the solution to dry.

The coating composition comprises polyurethane and a solvent. A suitable solvent for polyurethane can substantially, or preferably homogeneously dissolve the polyurethane; but the polyolefin is not dissolved in the solvent, at least not under the conditions of performing the present method. The person skilled in the art will be able to select a suitable solvent for a given polyurethane and polyolefin combination based on his general knowledge, optionally supported by some literature; for example based on solubility parameters of solvents and polymers, like given in the "Polymer Handbook" by Brandrup and Immergut, Eds. The skilled person is also aware of effects of polymer molar mass on solubility. For a so-called good solvent for a polyurethane including a TPU, interactions between polymer chain and solvent molecules are energetically favorable, and difference between solubility parameters of polymer and solvent is small. In present case of finding a solvent for the polyurethane that is a non-solvent for the polyolefin, the skilled person will realize that most polyurethanes as described herein above will have a more polar character than the polyolefin. In such case it is likely that a solvent that can dissolve polyurethane, for example assisted by stirring or sonication and optionally by applying some heating, will not dissolve the polyolefin when the solution of polyurethane is applied to the polyolefin construct.

In embodiments of the method, the solvent may be tetrahydrofuran (THF), methyl-tetrahydrofuran (m-THF), dimethylformamide (DMF), dimethylacetamide (DMAc), dimethylsulfoxide (DMSO), dichloromethane, chloroform, hexafluoro isopropanol, dioxane, dioxolane, mixtures thereof, or mixtures thereof with other less good solvents (or co-solvent), provided such mixtures can dissolve the polyurethane. In view of removing the solvent after application from the fibrous construct, a solvent having such volatility that solvent can be substantially removed by evaporation, optionally by heating to a temperature at least 10° C. below the melting point of the polyolefin, is preferred. In an embodiment, THF or m-THF is the solvent, preferably THF is the solvent.

The concentration of polyurethane in the solution applied in the solution coating step is not critical and will generally be in the range of 0.1-20 mass % of polyurethane based on the solution. It was observed in experiments, however, that if penetration of solution in voids or pores of the fibrous construct, i.e. impregnation of the polyolefin construct is desired, a solution of relatively low viscosity is preferably used. On the other hand, the higher the polyurethane concentration the less solution needs to be applied for effective coating while limiting impregnation. In embodiments, the solution of polyurethane elastomer may have a Brookfield viscosity of about 1-5000 mPa·s, or a viscosity of at least 5, 10, 25 or 50 mPa·s and at most 3000, 2000, 1000, or 500 mPa·s. Optimizing biological interactions of the composite biotextile can thus be done by varying coating conditions and locally or partially coating versus fully coating the surface of the construct with polyurethane.

The thermoplastic polyurethane that is applied in the method generally has at a certain temperature above its melting point, for example at the temperature locally reached during a later laser cutting step, a melt flow that is at least 10 times higher than the melt flow of the polyolefin; as further described herein above for the composite biotextile and illustrated with MFR, including the various optional or preferred embodiments.

The coating composition used in the method may further contain one or more auxiliary compounds, like radiopacifying agents (e.g., tantalum, tungsten, gold, platinum, iridium, etc), antibiotics, pharmacological agents to inhibit graft (re-)stenosis (e.g., Paclitaxel), or other biologics and small molecules to illicit a desired biological response. Such optional auxiliary compounds preferably have been approved for the targeted application by regulatory bodies like FDA; and may typically be present in relatively small, effective amounts, such that their concentration in the composite biotextile is effective for its purpose and within approved ranges, yet without unacceptably deteriorating other performance properties of the composite biotextile. If presence of a radiopacifier is desired in the polyurethane coating, such compound is preferably added to the coating composition by dispersing radiopacifier particles in the polyurethane solution; preferably using type and amounts of radiopacifier as described hereinabove.

The method of present disclosure further comprises a step of removing the solvent from the coated construct, preferably the solvent is substantially removed. A simple and preferred way is to evaporate the solvent (or solvent mixture). This may be performed at ambient conditions, but also by applying a reduced pressure and/or an elevated temperature to enhance efficiency. If an increased temperature is used, care should be taken to prevent deterioration of properties of the composite biotextile, for example caused by partial melting and/or stress relaxations of the polyolefin material. Preferably, the temperature applied remains well, for example at least 10° C., below the melting temperature of the polyurethane or TPU and of the polyolefin. Optionally, or alternatively, a washing step is applied to substantially remove the solvent. Washing can be done with a liquid comprising or consisting of a wash solvent that is a non-solvent for both the polyurethane and the polyolefin, but is miscible with the solvent for the polyurethane. Such washing step can be performed at ambient temperature, but also at elevated temperature with similar constraints as indicated above. Solvent removal is typically performed to result in a residual solvent level of the composite biotextile that is in accordance with specifications or regulations for use in a medical implant. In an embodiment, the composite biotextile has a residual solvent content of less than 50 ppm; for example after drying under nitrogen for 24 hours followed by drying in a convection oven at 50° C. for one hour.

In embodiments of the method, the polyolefin fibrous construct may be mounted in a holder or frame to keep the construct in its original form without notably tensioning the strands of the construct, and then be subjected to one or more of the steps of pretreating, solution coating and removing solvent. Advantages hereof may include more even pretreating and coating the construct, as well as preventing shrinkage, or deforming like wrinkling during e.g. coating and solvent removing steps. The skilled person will be able to select a suitable frame or alternative method of preventing the construct from deforming without hindering for example effectively coating at desired locations.

This method of the invention results in a composite polyurethane/polyolefin biotextile as described herein above, which biotextile is at least partially coated and/or impregnated with polyurethane.

The method of present disclosure may further comprise a step of cutting the composite biotextile as obtained at one or more coated locations with a laser, for example at a local cutting temperature above the melting point of polyurethane, to form a piece of composite biotextile of a desired shape and/or size, and having at least one stabilized cut edge. The skilled person will be able to select a suitable laser and settings thereof, to make a well-defined neat cut in the composite biotextile while preventing damage by overheating. As indicated in the above, preferred embodiments may apply a pulsed laser, preferably an ultra-short pulse laser (USP laser) like a nano-, pico- or femtosecond pulsed laser. In an embodiment, a cut is made using an USP laser with an energy level setting of about 10-26 W, preferably 12-24, 14-22 or 16-20 W and a cutting speed of 1-12 mm/s, preferably 2-10 or 3-8 mm/s. More than one scan with the USP laser may be needed to cut completely through the composite biotextile, o.a. depending on its thickness. In order to prevent damage to or distortion of the biotextile, multiple scanning steps may be preferred over using higher energy settings in a single scan.

In still further aspects, the invention concerns the use of such composite biotextile, especially a composite biotextile like a coated fabric having a stabilized (laser-)cut edge, in a medical implant component or as a medical implant component, especially for applications wherein the biotextile will be in contact with body tissue or fluids, such as in orthopedic or cardiovascular applications; like a mesh, a vascular graft, an occlusion device, a stent cover, or part of a prosthetic valve like a skirt or leaflet of a heart valve.

Other aspects include medical implants or medical devices, for example said orthopedic or cardiovascular devices, which devices comprise said medical implant component or said composite biotextile, especially such composite biotextile or fabric having a stabilized cut edge.

The use of the terms "a" and "an" and "the" and similar referents in the context of describing the invention (especially in the context of the following exemplary embodiments and claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, and each separate value is incorporated into the specification as if it were individually recited herein. The use of any and all examples, or exemplary language (e.g., "such as" or "like") provided herein, is intended merely to better illustrate the invention and does not pose a limitation on the scope of the invention unless otherwise claimed. No language in the specification should be construed as indicating any non-claimed element as essential to practicing the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The various aspects and ways of performing aspects of the invention as described above, are now further summarized by a series of exemplary embodiments.

1) A composite biotextile that comprises
   A polyolefin fibrous construct made from at least one strand with titer of 2-250 dtex, tensile strength of at least 10 cN/dtex and comprising high molar mass polyolefin fibers; and
   A coating comprising a biocompatible and biostable polyurethane elastomer comprising a polysiloxane in soft segments and/or having hydrophobic endgroups; wherein the polyurethane coating has been applied to at least part of the surface of the fibrous construct, and is present in an amount of 2.5-90 mass % based on composite biotextile.
2) A medical implant component comprising the composite biotextile of embodiment 1.
3) A method of making a composite biotextile for use in or as a medical implant component, the method comprising steps of
a. Providing a polyolefin fibrous construct made from at least one strand having titer of 2-250 dtex, tensile strength of at least 10 cN/dtex and comprising high molar mass polyolefin fibers;
b. Determining locations on the fibrous construct where a cut may be made for an intended use of the construct;
c. Optionally pretreating the fibrous construct at least at the determined locations with a high-energy source to activate the surface;
d. Solution coating the fibrous construct at least at the determined, and optionally pretreated, locations with a coating composition comprising a biocompatible and biostable polyurethane elastomer comprising a polysiloxane in soft segments and/or having one or more hydrophobic endgroups, and a solvent for the polyurethane; and
e. Removing the solvent from the coated fibrous construct; result in a composite biotextile with polyurethane coating on at least part of the surface of the biotextile, with polyurethane present in an amount of 2.5-90 mass % based on the composite biotextile.
4) The composite biotextile, medical implant component or method according to any one of embodiments 1-3, wherein the polyolefin fibrous construct comprises a rope, a cable, a tape, a textile, or a combination thereof.
5) The composite biotextile, medical implant component or method according to any one of embodiments 1-4, wherein the polyolefin fibrous construct comprises or consists of a polyolefin textile; preferably the textile is a fabric made by knitting, weaving, or braiding.
6) The composite biotextile, medical implant component or method according to any one of embodiments 1-5, wherein the polyolefin fibrous construct is a woven or knitted fabric, preferably a woven fabric.
7) The composite biotextile, medical implant component or method according to any one of embodiments 1-6, wherein the polyolefin fibrous construct is a woven fabric containing different warp and weft strands, and has anisotropic properties.
8) The composite biotextile, medical implant component or method according to any one of embodiments 1-3, wherein the strands of the fibrous construct have a titer of at most 225, 200, 180, 160, 140, 120, 100, 80, 60 or 50 dtex; and of at least 4, 5, 6, 8, 10, 15, or 20 dtex.
9) The composite biotextile, medical implant component or method according to any one of embodiments 1-8, wherein the polyolefin fibrous construct has a thickness of at most 300, 275, 250, 225, 200, 175, 150, 125, 100, 90, or 80 µm, and of at least 15, 20, 25, 30, 35, 40 45, or 50 µm.
10) The composite biotextile, medical implant component or method according to any one of embodiments 1-9, wherein the polyolefin fibrous construct has a substantially uniform or a non-uniform thickness.
11) The composite biotextile, medical implant component or method according to any one of embodiments 1-10, wherein the at least one strand of the polyolefin fibrous construct comprises at least one monofilament, typically with a titer of 2-50 dtex, or at least one, twisted or non-twisted, multi-filament yarn, typically with a yarn titer of about 2-250 dtex and containing filaments with filament titer of 0.2 to 5 dtex, preferably of 0.3-3 or 0.4-2 dtex per filament.
12) The composite biotextile, medical implant component or method according to any one of embodiments 1-11, wherein strands of the polyolefin fibrous construct comprise fibers are made from one or more polyolefins selected from homopolymers and copolymers containing one or more olefins as monomer units, which polyolefins have a weight averaged molar mass of at least 350 kDa.
13) The composite biotextile, medical implant component or method according to any one of embodiments 1-12, wherein strands of the polyolefin fibrous construct comprise polyolefin fibers made from a linear polyethylene such as a high molecular weight polyethylene (HMWPE), or an ultra-high molecular weight polyethylene (UHMWPE) having an intrinsic viscosity (IV) of between 4 and 40 dL/g.
14) The composite biotextile, medical implant component or method according to any one of embodiments 1-13, wherein strands of the polyolefin fibrous construct comprise UHMWPE fibers with a tensile strength of at least 15, 20, 25, 28, or 30 cN/dtex and typically of at most 40, 37 or 35 cN/dtex; preferably the UHMWPE fibers have a tensile modulus of 300-1500 cN/dtex.
15) The composite biotextile, medical implant component or method according to any one of embodiments 1-14, wherein strands of the polyolefin fibrous construct comprise at least 80 or 90 mass % of UHMWPE fibers, or substantially consist or consist of UHMWPE fibers.
16) The composite biotextile, medical implant component or method according to any one of embodiments 1-15, wherein the polyolefin fibrous construct comprises a combination of two or more different constructs; such as a combination of a textile and a rope, cable, or tape, or a combination of a woven fabric and a rope, cable, tape or non-woven.
17) The composite biotextile, medical implant component or method according to any one of embodiments 1-16, wherein the polyurethane elastomer is a thermoplastic or a thermoset polyurethane and soluble in a suitable solvent; preferably the polyurethane elastomer is a thermoplastic polyurethane (TPU).

18) The composite biotextile, medical implant component or method according to any one of embodiments 1-17, wherein the polyurethane coating layer is predominantly on a surface of the fibrous construct, such as on one side of a polyolefin fabric or on both sides of a polyolefin fabric.

19) The composite biotextile, medical implant component or method according to any one of embodiments 1-18, wherein the polyurethane coating is locally present at selected locations on the surface, or is present on substantially all surface area of the polyolefin construct.

20) The composite biotextile, medical implant component or method according to any one of embodiments 1-19, wherein the polyurethane coating layer partially or fully covers the fibers in the construct, to result in a partially or fully polyurethane-impregnated fibrous construct.

21) The composite biotextile, medical implant component or method according to any one of embodiments 1-20, wherein the polyurethane elastomer comprises soft blocks derived from at least one aliphatic polymer diol, chosen from the group consisting of polyethers, polyesters, polyacrylates, polyolefins and polysiloxanes, 22) The composite biotextile, medical implant component or method according to any one of embodiments 1-21, wherein the polyurethane elastomer comprises soft blocks derived from a polysiloxane diol such as a poly(dimethyl siloxane) diol, an aliphatic polyether like a poly(tetramethylene oxide) diol, an aliphatic polyester, like an aliphatic polycarbonate such as a poly(hexamethylene carbonate) diol or a poly(polytetrahydrofuran carbonate) diol, or a combination thereof.

23) The composite biotextile, medical implant component or method according to any one of embodiments 1-22, wherein the polyurethane elastomer comprises soft blocks derived from a polysiloxane diol and one or more of a polycarbonate diol and a poly(tetramethylene oxide) diol.

24) The composite biotextile, medical implant component or method according to any one of embodiments 1-23, wherein the polyurethane elastomer comprises soft blocks having a molar mass ($M_n$) of 200 to 100,000 Da, preferably at least 400, 600, 800 or 1000 Da and at most 10000, 7500, 5000, 4000, 3000 or 2500 Da.

25) The composite biotextile, medical implant component or method according to any one of embodiments 1-24, wherein the polyurethane elastomer has a Shore hardness of at least 40, 50 or 60 ShA and at most 80, 70, or 60 ShD or at most 100, 90 or 85 ShA.

26) The composite biotextile, medical implant component or method according to any one of embodiments 1-25, wherein the polyurethane elastomer is linear and comprises a hydropobic endgroup at least at one chain end, and preferably comprises an average of two hydropobic endgroups.

27) The composite biotextile, medical implant component or method according to any one of embodiments 1-26, wherein the polyurethane elastomer has at least one hydrophobic endgroup comprising a $C_2$-$C_{20}$ alkyl, a $C_2$-$C_{1e}$ fluoroalkyl, a $C_2$-$C_{1e}$ fluoroalkyl ether, a hydrophobic poly(alkylene oxide), or a polysiloxane, like a poly(dimethyl siloxane), preferably at least one endgroup comprising a polysiloxane.

28) The composite biotextile, medical implant component or method according to any one of embodiments 1-27, wherein the hydrophobic endgroup is monomeric and has a molar mass of at least 200, 300, or 500 Da and at most 1,000 or 800 Da.

29) The composite biotextile, medical implant component or method according to any one of embodiments 1-27, wherein the hydrophobic endgroup is polymeric and has a molar mass of at least 500, 1000, or 2000 Da and at most 10000, 8000, 6000 or 4000 Da.

30) The composite biotextile, medical implant component or method according to any one of embodiments 1-29, wherein the hydrophobic endgroup is present in an amount of at least 0.1, 0.2, 0.3, 0.4 or 0.5 mass %, and at most 4, 3, 2 or 1 mass %, based on the total mass of the polyurethane.

31) The composite biotextile, medical implant component or method according to any one of embodiments 1-30, wherein the coating comprises a TPU that shows at a temperature above its melting point a melt flow that is at least 10 times higher than the melt flow of the polyolefin at said temperature; for example at 210-240° C. the TPU has a melt flow index that is at least 10, 20, 40, 60 or even 100 times the melt flow index of the polyolefin.

32) The composite biotextile, medical implant component or method according to any one of embodiments 1-31, wherein the polyolefin fibrous construct is a textile like a fabric, and the polyurethane coating is present on at least part of the surface of at least one side of the construct.

33) The composite biotextile, medical implant component or method according to any one of embodiments 1-31, wherein the polyurethane coating is present on substantially all surface area of the fibrous construct, like on both sides of a polyolefin textile.

34) The composite biotextile, medical implant component or method according to any one of embodiments 1-33, wherein the polyurethane is present as a surface coating and/or has impregnated the fibrous construct.

35) The composite biotextile, medical implant component or method according to any one of embodiments 1-34, wherein the polyurethane coating is present in the form of one or more stripes, preferably having a width of at least 1, 2 or 3 mm and at most 10, 8, 6, 5, or 4 mm.

36) The composite biotextile, medical implant component or method according to any one of embodiments 1-35, wherein polyurethane is present in an amount of at least 5, 10, 15, 20 or 25 mass %, and of at most 80, 70, 60, 50, 40 or 30 mass %.

37) The composite biotextile, medical implant component or method according to any one of embodiments 1-36, wherein polyurethane is present in an amount of at least 0.2, 0.5, 1.0, 1.5, 2.0 or 2.5 mg/cm$^2$ and of at most 9, 8, 7, 6, or 5 mg/cm$^2$ 38) The composite biotextile, medical implant component or method according to any one of embodiments 1-37, wherein the composite biotextile is a textile with a thickness of at most 325, 300, 275, 250, 225, 200, 175, 150, 125, 100, 90, or 80 μm, and of at least 20, 25, 30, 35, 4045, or50 μm.

39) The composite biotextile or medical implant component according to any one of embodiments 1-38, wherein the composite biotextile has at least one cut edge that is coated and/or impregnated with the polyurethane elastomer 40) The composite biotextile or medical implant component according to embodiment 39, wherein the composite biotextile has a suture retention strength at the cut edge of at least 15, 20, 22 or 24 N and of at most 50, 45 or 40 N; preferably the polyolefin fibrous construct is a textile, preferably a fabric.

41) The method according to any one of embodiments 1-38, wherein the optional step of pretreating the fibrous construct at least at the determined locations is a plasma or corona treatment, for example a cold plasma treatment performed at atmospheric or reduced pressure and at a temperature that does not negatively affect the polyolefin fibrous construct.

42) The method according to embodiment 39, wherein the fibrous construct is a textile with two opposite surfaces, and pretreating is done at least at the determined locations on at least one side of the textile, preferably on both sides at opposing and corresponding locations of the textile.

43) The method according to any one of embodiments 41-42, wherein pretreating is performed to activate substantially all surface of the fibrous construct.

44) The method according to any one of embodiments 41-43, wherein solution coating is done with a coating composition comprising polyurethane that is dried to a level of less than 0.05 mass % of water before dissolving in solvent.

45) The method according to any one of embodiments 41-44, wherein solution coating is done by using a pipette or a syringe, by dip-coating, by spray coating, by ink jet application, or by a combination thereof.

46) The method according to any one of embodiments 41-45, wherein solution coating is done in one step, or in multiple steps with preferably a certain drying time between steps.

47) The method according to any one of embodiments 41-46, wherein the coating composition comprises a solvent that can dissolve the polyurethane but not the polyolefin; preferably the solvent is selected from tetrahydrofuran (THF), methyl-tetrahydrofuran (m-THF), dimethylformamide (DMF), dimethylacetamide (DMAc), dimethylsulfoxide (DMSO), dichloromethane, chloroform, hexafluoro isopropanol, dioxane, dioxolane, mixtures thereof, or mixtures thereof with other less good solvents.

48) The method according to any one of embodiments 41-47, wherein the coating composition has a Brookfield viscosity of at least 1, 5, 10, 25 or 50 mPa·s and at most 5000, 3000, 2000, 1000, or 500 mPa·s. about 1-5000 mPa·s.

49) The method according to any one of embodiments 41-48, wherein removing the solvent is done by evaporation or washing, preferably solvent is substantially removed at ambient conditions or at a temperature at least 10° C. below the melting temperatures of the polyurethane and the polyolefin.

50) The method according to any one of embodiments 41-49, wherein removing the solvent results in a composite biotextile with a residual solvent content of less than 50 ppm.

51) The method according to any one of embodiments 41-50, further comprising a step of laser cutting the composite biotextile according to any one of embodiments 1-38 or as obtained by method according to any one of embodiments 41-50 at at least one location where polyurethane is present, to result in a piece of composite biotextile of desired shape and/or size, and having a stable cut edge.

52) The method according to embodiment 51, wherein laser settings are selected such that no excessive heating of the composite biotextile occurs, to result in a well-defined, regular and clean cut edge.

53) The method according to any one of embodiments 51-52, wherein laser cutting is done with pulsed laser, preferably with a short pulse or ultra-short pulse laser, like a nano-, pico-, or femtosecond pulsed laser.

54) The method according to any one of embodiments 51-53, wherein laser cutting is done with a pulsed laser with an energy level setting of 10-26 W, preferably 12-24, 14-22 or 16-20 W and a cutting speed of 1-12 mm/s, preferably of 2-10 or 3-8 mm/s.

55) The method according to any one of embodiments 51-54, wherein laser cutting at a location is done with multiple laser scanning steps.

56) Use of a composite biotextile according to any one of embodiments 1 and 3-40 or as obtained by the method according to any one of embodiments 41-55, in making a medical implant component or a medical implant, like a mesh, a vascular graft, an occlusion device, a stent cover, or a skirt or leaflet of a prosthetic valve such as a heart valve.

57) Use according to embodiment 56, wherein the composite biotextile will be in contact with body tissue or fluids, such as in orthopedic applications including meshes for tissue reinforcement procedures or in cardiovascular devices like a vascular graft, a stent cover, or a prosthetic valve like a venous valve or heart valve.

58) A medical implant or medical device comprising a composite biotextile according to any one of embodiments 1 and 3-40 or as obtained by the method according to any one of embodiments 41-55, preferably comprising such composite biotextile having at least one stabilized cut edge.

59) The medical implant or medical device according to embodiment 58 for use in orthopedic or cardiovascular applications.

The experiments and samples below further elucidate embodiments of the invention, but of course, should not be construed as in any way limiting the scope of the claims.

EXAMPLES AND COMPARATIVE EXPERIMENTS

Materials

The polyolefin textile used as starting material in the experiments was a woven fabric with 2*2 twill weave pattern, of 45 mm flat width and thickness of about 70 μm, made from a medical grade, low-denier UHMWPE multifilament yarn as warp and weft strands (Dyneema Purity® TG 10 dtex; available from DSM Biomedical BV, Sittard-Geleen NL).

As polyurethane elastomer following grades were used (available from DSM Biomedical BV, Sittard-Geleen NL):
CarboSil® TSPCU 20-80A; a thermoplastic silicone polycarbonate polyurethane, comprising silicone in soft segments and having silicone endgroups, hardness 80 ShA, and MFR 52 g/10 min (1.20 kg/224° C.);
Biospan® S SPU, a segmented polyether urethane comprising urea groups and having silicone end groups, hardness about 74 ShA.

A medical grade microporous UHMWPE film (Dyneema Purity® membrane, available from DSM Biomedical BV, Sittard-Geleen NL) having thickness of about 15 μm and porosity of 83 vol % was used to laminate with woven fabric.

Methods

Solution Viscosity

Solution viscosity at 25° C. is determined with a Brookfield DV-E viscometer with UL-adaptor and ULA-49EAY spindle, which is calibrated using silicone-based viscosity standards (Benelux Scientific).

Dip-Coating

Fabric samples of about 10-20 cm length are cut from the continuous woven UHMWPE fabric of about 45 mm width (described above); washed in heptane for 1 minute and dried at 40° C.; and then mounted length-wise at the short sides in a frame as sample holder.

Framed samples are pretreated by plasma activation during 60 s in a 15% oxygen atmosphere at 200 mTorr and 450 W.

Dip-coating is performed at ambient conditions by submersing a framed sample in a polymer solution and removing the samples with take-up speed of 0.1 m/sec; followed by drying at 40° C. for 20 minutes.

Fabric Thickness

Thickness of a fabric is measured using a Helios Preisser Electronic Outside Micrometer, with measuring range 0-25 mm (±0.001 mm).

Suture Retention Strength

Suture retention strength is measured on pieces of fabric of about 30*10 mm, through which a high-strength suture (FiberWire® 4.0) was inserted with a low-profile tapered needle in the center of the fabric and 2 mm from the edge of the short side. A Zwick Universal testing machine is used, equipped with a pneumatic Instron Grip (7 bar) and a Grip G13B, between which the looped suture and other end of the fabric are mounted with 50 mm grip-to-grip distance and preload of 0.05 N. The suture is then tensioned at test speed of 50 mm/min until failure of the sample. Suture retention strength is reported as the yield point of the measured pull out stress-strain curve (average+/−std; for 3 measurements), that is the force needed to pull the looped suture through the edge zone of the fabric.

Abrasion Resistance

Abrasion resistance of samples is tested using a Martindale 900 series Abrasion and Pilling Tester (James H Heal & Co. Ltd), applying ISO 12947-2 and ASTM D4966 as guidance. Half-moon shaped samples, matching the size of the circular sample holders of the tester were laser-cut from pieces of fabric, with the long edge in the warp direction. Samples are mounted in the specimen holders and rubbed with a forward- and backward translational movement or cycle (along the linear cut edge of a half-moon sample at 56 cycles/min) against a standard fabric (Abrasive cloth SM25, circular patch of 140 mm diameter) as abradant under 9 kPa loading weight. Samples (and micrographs thereof as taken with a Tagarno digital microscope at about 100* magnification) are visually inspected on wear, pilling, or other damage after 500, 1000, 2000, 3000, 4000, 8000, 10000 and 15000 cycles (for- and backward movements).

Hemocompatibility

Blood contact properties of samples are evaluated with the Chandler Blood Loop in vitro model. This closed system model has been reported in literature (DOI: doi: 10.1007/s10856-011-4335-2.) and is designed to investigate the effect of artificial surfaces to initiate the different and complex cascade of reactions intrinsic to human blood organ (e.g., coagulation, cell alteration, complement and inflammation). The model is in alignment with ISO 10993-4:2002. The Chandler Loop model provides material characteristics across a panel of hemocompatibility criteria, including thrombogenicity, coagulation, platelet number and activation, hemolysis, leukocyte activation, and complement activation. Whole blood from healthy donors is carefully drawn and minimally heparinized, and then gently circulated in rotating heparinized PVC tubing containing the test samples for 90 minutes in a thermostatic bath maintained at 37° C. Blood with no material contact is used as an internal model control; blood in contact with only the heparinized PVC tubing is used as a control. Blood is not pooled between donors but rather represents separate experiments, to be averaged at the end of the study. After 90 minutes incubation, test samples and circulating blood are collected and may be subjected to following analyses:

Thrombogenicity is analyzed by scanning electron microscopy on the test sample surfaces. Fibrin, platelet, and leukocyte adhesion to the surface is observed and compared between groups;

Coagulation is measured immunochemically (e.g., ELISA) targeting coagulation factors XII, XI, and X—all of which modulate prothrombin conversion and clotting. Thrombin-antithrombin-III complex is also measured as a sensitive marker of coagulation activation;

Platelet count is measured in the circulated blood using a cell counter;

Quantifying a deficit in platelets in the circulating blood due to exposure to material surfaces indicates perturbation of the platelet behavior due to low hemocompatibility. Platelet activation marker β-thromboglobulin is measured by ELISA;

Red and white blood cell count is measured using a cell counter and is a general descriptor of hematologic effect;

Hemolysis is quantified by measuring free hemoglobin content in the blood using a colorimetric biochemical assay;

Leukocyte activation is assayed by quantifying the enzymatic marker PMN-Elastase; and/or Complement activation is assayed by quantifying SC5b-9 marker of complement complexation.

This panel of readouts typifies the blood contact properties of each material and an indication of the hemocompatibility of the composite materials can be made.

Sample Preparation and Suture Retention
(Comparative Experiments 1-3 and Examples 4-6)

Suture retention strength of sample pieces of 100*30 mm that were laser cut from the non-modified UHMWPE fabric in both length (warp) and width (weft) directions were measured. Results summarized in Table 1 as comparative experiment 1 (CE1) relate to testing in weft direction; results obtained in warp direction were comparable.

The fabric pieces as cut with an ultra-short pulsed laser (USP laser; operated at 800 kHz, at 18 W, and cutting speed 5 mm/s) have straight and well-defined sharply cut edges. An example of such cut edge is shown in FIG. 1A, micrograph taken with a Tagarno digital microscope at about 150* magnification). An inserted suture, however, is rather easily pulled through the raveling fabric. Using higher energy upon laser cutting with a $CO_2$ laser operated in continuous mode at a low (10% of 100 W maximum power, cutting speed 35 mm/s; CM laser—low) and a higher setting (20% power, cutting speed 35 mm/s; CM laser—high) resulted in higher suture retention strength; but the cut edges of the fabric, however, are found to be unacceptably irregular with local thickening of partially molten and re-solidified fibers. The cut edges also feel rough to the fingers and stiffer than the fabric itself.

Figure 2:
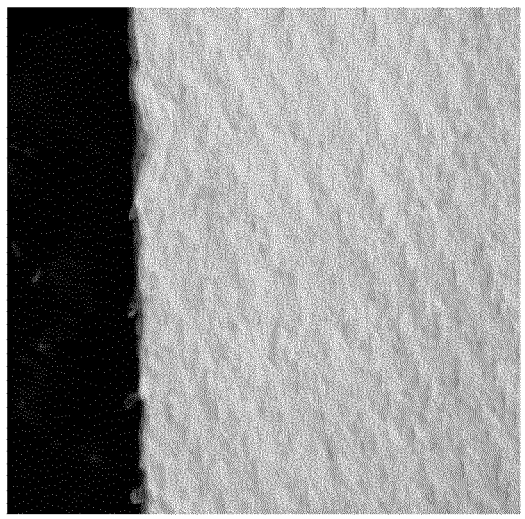
FIGS. 2A and 2B represent micrographs showing the laser-cut edge of UHMWPE laminated fabric (CE2), as made with USP (2A) and CM lasers (2B).
Figure 2:
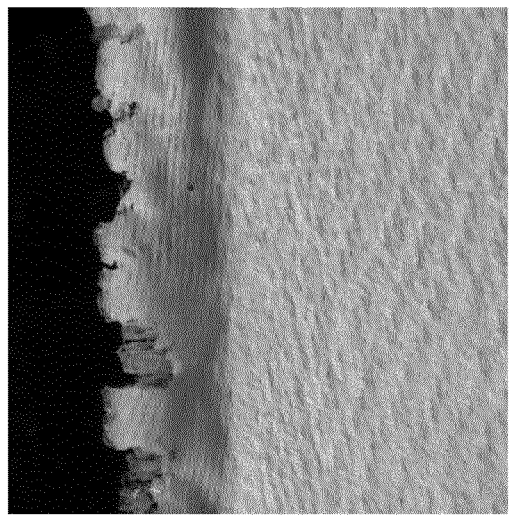

In comparative experiment 2 the UHMWPE fabric was heat-laminated at both sides by sandwiching between two sheets of microporous UHMWPE film (Dyneema Purity® membrane). The sandwich was placed between Teflon sheets in a hot platen press, heated for 10 min at 140° C. and 50 kN pressure, and cooled under pressure to room temperature in 15 minutes. Suture retention testing data for this CE2 fabric (see Table 1) indicates some strength increase when cut with ultra-short pulsed laser, and significantly improved strength for samples cut with higher energy $CO_2$ laser operated in continuous mode. Micrographs of the cut edges show irregular edges with lumps of molten and re-solidified material, increasing from pulsed to high intensity continuous mode laser cutting (see examples in FIG. 2). The thickness of the composite fabric indicates that the materials were densified, and the modified fabric is markedly less flexible and pliable than the starting polyolefin fabric.

In experiment CE3 the UHMWPE fabric was treated with a $CO_2$ CM laser to weld the strands in the fabric together by partially melting, contacting and re-solidifying the surfaces. A piece of the fabric was laser treated to make fused zones, such that subsequently samples of desired size could be made using a USP laser; the samples having a fused edge zone of at least about 3 mm. Suture retention strength was found to be higher than for non-modified fabric, but not at the level found for CE2 samples (see Table 1).

Figure 3:
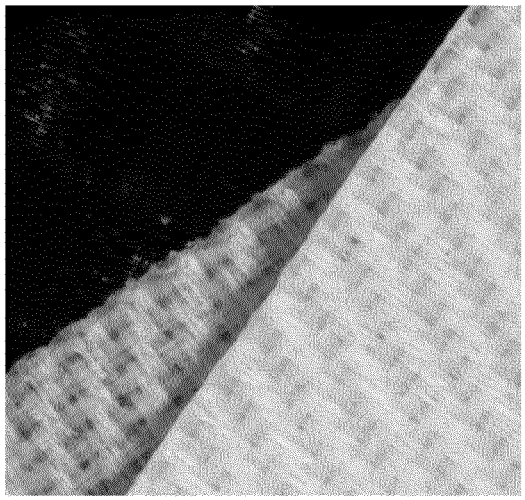
FIGS. 3A and 3B show the laser-cut edges of polyurethane-coated UHMWPE fabric (Ex4), as made with USP laser (3A) and CM laser (3B).
Figure 3:
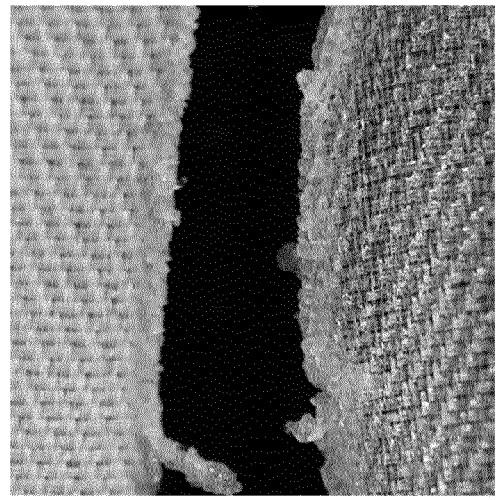
Figure 4:
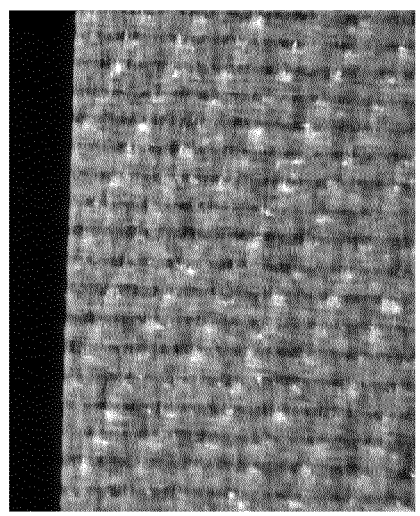
FIGS. 4A and 4B show the laser-cut edges of other polyurethane-coated UHMWPE fabrics, as made with USP laser from sample Ex5 (4A) and with CM laser from 1-layer and 2-layer coated fabrics Ex5 and Ex6 (4B).
Figure 4:
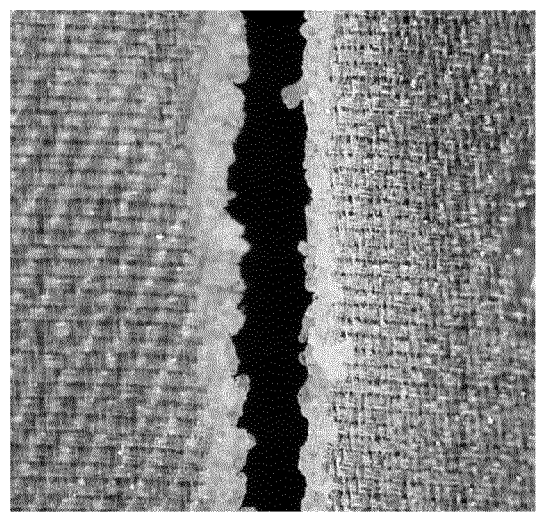

In Example 4 the UHMWPE fabric was dip-coated in one step with a 10 mass % solution of a CarboSil® TSPCU 20-80A in THF (Lichrosolve); prepared by first drying the polyurethane pellets overnight at 70° C. and then stirring THF and pellets overnight at room temperature. This solution was found to have a Brookfield viscosity of about 180 mPa·s. Samples for suture retention testing were made with different (settings of) lasers as above; and results for testing in weft direction are in Table 1 (Ex4). This polyurethane-coated UHMWPE fabric shows markedly increased resistance to raveling when laser cut, seemingly independent of laser energy applied. The resulting edges, however, are dependent on the type of laser cutting: edges resulting from controlled energy cutting with a USP laser, at different settings, are well-defined and regular; whereas CM laser cutting produces irregular edges and stiffening. In FIG. 3 this is illustrated with some micrographs. FIG. 3A shows edges made with a USP laser applying 2 different energy levels, FIG. 3B is made of fabric edges resulting from cutting with a CM laser at low (left) and high settings (right). It will be clear that sample Ex4 produced via USP laser cutting is to be preferred for medical implant applications, for example because irregular edges may not only cause irritation after implantation but can also initiate further damage or failure of the composite fabric upon extended use while being flexed etc.

These experiments thus demonstrate that a combination of providing a specific polyurethane coating to the fabric and cutting with a pulsed laser will enable making an improved composite fabric that is suitable for use as an implant component that has proper suture retention strength.

In Experiments 5 and 6 the UHMWPE fabric was dip-coated with an 8 mass % solution of pre-dried Biospan® S SPU polyurethane in DMAc (Brookfield viscosity of about 220 mPa·s), by applying 1 layer (Ex5) and after intermediate drying a $2^{nd}$ layer of polyurethane (Ex6). Analogous to the observations for Ex4, USP laser cutting of coated fabric results in a composite fabric having stabilized and well-defined smooth edges, not showing the irregularities and thickening that occur upon laser cutting with a continuous mode laser.

TABLE 1

Suture retention strength

| | Sample | | | Suture retention strength (N) | | |
|---|---|---|---|---|---|---|
| # | Type of coating | Amount of coating (mass %) | Thickness (μm) | Cut with USP laser | Cut with CM laser-low | Cut with CM laser-high |
| CE1 | None | — | 70 | 13.9 ± 3.0 | 43.5 ± 2.7 | 49.5 ± 5.1 |
| CE2 | Laminated with 2 sheets of PE film | — | 81 | 22.9 ± 3.1 | 44.8 ± 4.9 | 39.0 ± 5.6 |
| CE3 | None; Laser welded | — | — | 25.3 ± 0.8 | nd | nd |
| Ex4 | Carbosil, 1 coat | 40.2 | 75 | 39.8 ± 3.1 | 40.1 ± 4.0 | 37.5 ± 5.6 |
| Ex5 | Biospan, 1 coat | 43.3 | 73 | 24.0 ± 3.4 | 28.5 ± 8.3 | 33.3 ± 6.7 |
| Ex6 | Biospan, 2 coats | 59.1 | 81 | 28.2 ± 5.9 | 34.8 ± 4.3 | 32.0 ± 6.4 |

Abrasion Resistance (CE7 and Ex8-10)

Abrasion resistance was determined as indicated above on samples as listed in Table 2, which samples correspond to those used in CE2 and Ex4-6 and were cut to size using the USP laser; resulting in straight and clean cut edges.

Figure 5:
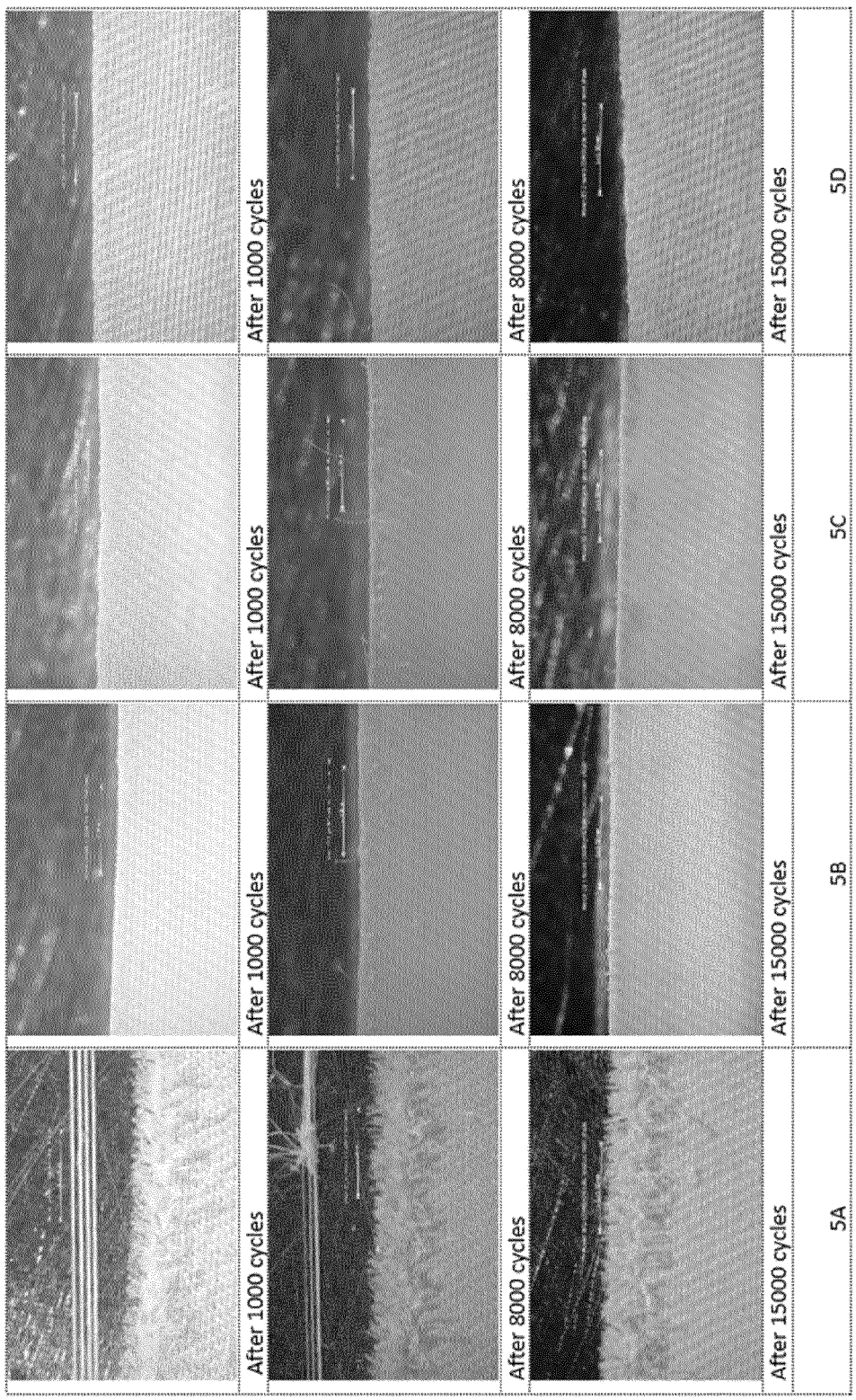
FIGS. 5A-5D show photo micrographs of the laser-cut edge part of samples having been exposed to abrasion testing; for uncoated UHMWPE fabric (CE7.

As summarized in Table 2, the unmodified woven sample CE7 showed already significant fraying and non-bound warp strands at the cut edge after 500 cycles, and broken filaments on the surface of the fabric. During further abrading cycles, damaging continued with loose filaments, increased fraying and unraveling, and 'released' warp yarns at the edge being broken and pull away. Three examples of micrographs of edges (at about 100* magnification) are shown in FIG. 5A. In contrast thereto, the coated fabrics showed markedly better resistance to fraying when submitted to the abrasion test. During testing of Example 8 (with Carbosil® coating) some broken filaments, indicating initial stage of fraying, were observed after 8000 cycles; but also after 15000 cycles only few damaged filaments at the edge were visible. Similarly, Examples 9 and 10, with 1 or 2 layers of Biospan® coating, showed only some broken filaments and hardly any fraying after 15000 cycles; see also Table 2 and FIGS. 5C-D.

TABLE 2

Abrasion testing

| | Sample | | Abrasion resistance | | |
|---|---|---|---|---|---|
| | Type | Amount of | (Observations after number of cycles) | | |
| # | of coating | coating (mass %) | 1000 cycles | 8000 cycles | 15000 cycles |
| CE7 | none | — | Significant fraying; free warp | Severe fraying; damaged weft and warp | Severe fraying; damaged weft strands, broken |

TABLE 2-continued

Abrasion testing

| # | Sample Type of coating | Amount of coating (mass %) | Abrasion resistance (Observations after number of cycles) | | |
|---|---|---|---|---|---|
| | | | 1000 cycles | 8000 cycles | 15000 cycles |
| | | | strands | strands | filaments, outer warp strand gone |
| Ex8 | Carbosil | 40.2 | No visible change | Some damaged filaments | Very limited fraying |
| Ex9 | Biospan 1* | 43.3 | No visible change | Some damaged filaments | Very limited fraying |
| Ex10 | Biospan 2* | 59.1 | No visible change | Few damaged filaments | Very limited fraying |

Hemocompatibility (CE11-12 and Ex13-15)

In these experiments, above-mentioned materials and a reference woven material, based on polyethylene terephthalate yarn (PET), were tested for their hemocompatibility in a Chandler Blood Loop in vitro model using human blood, as described above. The materials tested and a summary of results are provided in Table 3.

The commercially available PET woven (e.g. available as Dacron®, used as an aortic stent graft covering) was manually cut to sample size and used in CE11 as reference material. The non-coated UHMWPE fabric (same as above) was used in CE12. Examples 13-15 concern coated UHMWPE fabric, analogous to above Examples; test specimen of 5*80 mm were laser cut from larger pieces. All samples were sterilized twice with ethylene oxide prior to Chandler Loop testing. Blood circulating in heparinized PVC tubing and containing no test material served as an internal control for the model itself.

All samples were individually tested in blood attained from five healthy human donors. Red and white blood cell counts, as well as levels of free plasma hemoglobin, hemoglobin, hematocrit, and SC5b-9 complement activation were found to be similar and stable within all materials. The results from each assay, wherein notable differences were observed between tested materials, are listed in Table 3; numbers given represent the mean value+/−the standard deviation (n=6).

Biologically relevant improvement in hemocompatibility between coated and non-coated UHMWPE was observed in thrombin-antithrombin complexes (TAT) concentration, demonstrating that both polyurethane coatings reduced the thrombogenicity, i.e blood coagulation activation, of the UHMWPE fabric according to this specific coagulation marker. All materials showed elevated TAT levels vs the control, but the uncoated and coated UHMWPE fabrics evoked 85-97% lower levels than the PET woven.

Other important differences were observed when comparing coated and uncoated UHMWPE versus PET. Specifically, platelet count was reduced for all samples, but was at significantly higher level for the (coated) UHMWPE materials than for PET woven. Levels of the platelet activation marker β-thromboglobulin (β-TG) were more than a factor 2 higher for PET than for uncoated and coated UHMWPE materials. The UHMWPE fabric twice coated with Biospan® polyurethane showed best performance in this assay. Finally, PMN-elastase, a pathologic indicator of granulocyte activation, was almost 2* higher for PET than for (uncoated and coated) UHMWPE fabrics.

TABLE 3

Hemocompatibility evaluation

| | Sample | Results of in-vitro Chandler Loop model testing | | | |
|---|---|---|---|---|---|
| # | Type of sample | TAT (µg/l) | Platelet count ($10^3$/µl) | β-TG (IU/ml) | PMN-elastase (ng/ml) |
| Control | PVC tube | 93 ± 53 | 188 ± 24 | 906 ± 757 | 54 ± 35 |
| CE11 | PET woven; no coating | 6374 ± 2759 | 103 ± 40 | 4192 ± 496 | 122 ± 40 |
| CE12 | UHMWPE woven; no coating | 1429 ± 857 | 165 ± 21 | 1881 ± 336 | 68 ± 14 |
| Ex13 | UHMWPE woven; Carbosil coating (1 layer) | 318 ± 119 | 160 ± 27 | 1919 ± 996 | 69 ± 31 |
| Ex14 | UHMWPE woven; Biospan coating (1 layer) | 350 ± 229 | 170 ± 22 | 1922 ± 844 | 71 ± 36 |
| Ex15 | UHMWPE woven; Biospan coating (2 layers) | 352 ± 188 | 172 ± 27 | 1459 ± 560 | 76 ± 26 |

These in vitro hemocompatibility results demonstrate, the measured levels in several assays being comparable for (coated) UHMWPE fabric samples and the heparinized PVC tube containing no test material (internal control), that the present composite biotextiles show favorable hemocompatibility. The coated and uncoated UHMWPE fabrics even can be concluded to present superior hemocompatibility over the PET fabric that is frequently used in blood contact applications like stent-grafts.

The invention claimed is:

1. A medical implant component comprising a composite biotextile, wherein the biotextile comprises:
   a polyolefin fibrous construct comprising at least one strand with a titer of 2-250 dtex, a tensile strength of at least 10 cN/dtex and comprising high molar mass polyolefin fibers;
   and a coating comprising a biocompatible and biostable polyurethane elastomer comprising soft segments of a polysiloxane and/or comprising at least one hydrophobic end group; wherein the coating is present on at least part of the surface of the fibrous construct, and is present in an amount of 2.5-90 mass % based on the total mass of the composite biotextile.

2. The medical implant component according to claim 1, wherein the fibrous construct has anisotropic properties, wherein the anisotropy of the fibrous construct is a result of a combination of at least two different strands in the fibrous construct, and/or from a combination of at least two of a rope, a cable, a tape, and a textile in the fibrous construct.

3. The medical implant component according to claim 1, wherein the at least one strand has a titer of 4-140 dtex.

4. The medical implant component according to claim 1, wherein the polyolefin fibrous construct has a thickness of about 15-300 µm.

5. The medical implant component according to claim 1, wherein the polyolefin is ultra-high molecular weight polyethylene (UHMWPE).

6. The medical implant component according to claim 2, wherein strands of the polyolefin fibrous construct comprise UHMWPE fibers with a tensile strength of at least 15 and at most about 40 cN/dtex.

7. The medical implant component according to claim 5, wherein strands of the polyolefin fibrous construct comprise UHMWPE fibers with a tensile strength of at least 20 and at most 35 cN/dtex.

8. The medical implant component according to claim 1, wherein strands of the fibrous construct comprise at least 80 mass % of UHMWPE fibers based on the total mass of the fibrous construct.

9. The medical implant component according to claim 1, wherein the polyurethane elastomer comprises a thermoplastic polyurethane comprising a combination of i) a polyether and a polysiloxane or ii) a polycarbonate and a polysiloxane.

10. The medical implant component according to claim 1, wherein the polyurethane elastomer has a hardness from 40-100 ShA.

11. The medical implant component according to claim 1, wherein the hydrophobic end group comprises a C2-C20 alkyl, a C2-C16 fluoroalkyl, a C2-C16 fluoroalkyl ether, a hydrophobic poly(alkylene oxide) or a polysiloxane.

12. The medical implant component according to claim 1, wherein the polyolefin fibrous construct comprises a textile and the polyurethane coating is present on substantially all surface area of both sides of the polyolefin fibrous construct.

13. The medical implant component according to claim 1, wherein the polyurethane coating is present at a cut edge of the composite biotextile,
and wherein the composite biotextile has a suture retention strength at said cut edge of 15-50 N, as measured with the method described in the experiments.

14. The medical implant component according to claim 1, wherein the polyolefin fibrous construct comprises a knit, woven, or braided fabric.

15. The medical implant component according to claim 1, wherein the polyolefin fibrous construct comprises a woven fabric.

16. The medical implant component according to claim 1, wherein the at least one strand has a titer of 6-100 dtex.

17. The medical implant component according to claim 1, wherein the at least one strand has a titer of 8-60 dtex.

18. The medical implant component according to claim 1, wherein the polyurethane elastomer comprises a hydrophobic end group and the hydrophobic end group comprises a polysiloxane.

19. A prosthetic heart valve comprising the medical implant component according to claim 1.

20. A method of making a composite biotextile for use in or as a medical implant component, the method comprising steps of:
(a) providing a polyolefin fibrous construct comprising at least one strand having titer of 2-250 dtex, a tensile strength of at least 10 cN/dtex and comprising high molar mass polyolefin fibers;
(b) solution coating the fibrous construct with a coating composition comprising a biocompatible and biostable polyurethane elastomer comprising soft segments of a polysiloxane and/or having at least one hydrophobic end group and a solvent for the polyurethane;
(c) removing the solvent from the coated fibrous construct, thereby forming a composite biotextile; and
(d) optionally laser cutting the composite biotextile at least at one coated location.

* * * * *